(12) United States Patent
Bobde et al.

(10) Patent No.: US 12,033,725 B2
(45) Date of Patent: Jul. 9, 2024

(54) ANTIMICROBIAL PEPTIDES AND RELATED METHODS

(71) Applicant: GEORGE MASON UNIVERSITY, Fairfax, VA (US)

(72) Inventors: Shravani Bobde, Arlington, VA (US); Monique Van Hoek, Fairfax, VA (US)

(73) Assignee: GEORGE MASON UNIVERSITY, Fairfax, VA (US)

( * ) Notice: Subject to any disclaimer, the term of this patent is extended or adjusted under 35 U.S.C. 154(b) by 0 days.

(21) Appl. No.: 17/822,161

(22) Filed: Aug. 25, 2022

(65) Prior Publication Data

US 2023/0074829 A1 Mar. 9, 2023

Related U.S. Application Data

(60) Provisional application No. 63/236,805, filed on Aug. 25, 2021.

(51) Int. Cl.
| | |
|---|---|
| C07K 7/08 | (2006.01) |
| A01N 37/46 | (2006.01) |
| A01P 1/00 | (2006.01) |
| A61K 38/00 | (2006.01) |
| A61P 31/04 | (2006.01) |
| G16B 30/00 | (2019.01) |
| G16B 40/00 | (2019.01) |
| G16B 50/00 | (2019.01) |

(52) U.S. Cl.
CPC ............ *G16B 40/00* (2019.02); *A01N 37/46* (2013.01); *A01P 1/00* (2021.08); *A61P 31/04* (2018.01); *C07K 7/08* (2013.01); *G16B 30/00* (2019.02); *G16B 50/00* (2019.02); *A61K 38/00* (2013.01)

(58) Field of Classification Search
CPC ........ G16B 40/00; G16B 30/00; G16B 50/00; A61P 31/04; A01P 1/00; A01N 37/46; C07K 7/08; A61K 38/00
See application file for complete search history.

(56) References Cited

U.S. PATENT DOCUMENTS

9,597,407 B2 * 3/2017 Eckert .................... A61K 38/08

FOREIGN PATENT DOCUMENTS

WO WO-2015029031 A1 * 3/2015 ........... C07K 14/415

OTHER PUBLICATIONS

Wang et al., Identification and functional analyses of novel antioxidant peptides and antimicrobial peptides from skin secretions of four East Asian frog species, Acta Biochim Biophys Sin, 49(6), 550-559 doi: 10.1093/abbs/gmx032. (Year: 2017).*
Search Results Feb. 21, 2023, Generated by ABSS submission. (Year: 2023).*

(Continued)

*Primary Examiner* — Kevin S Orwig
*Assistant Examiner* — John Michael Cronin
(74) *Attorney, Agent, or Firm* — Debora Plehn-Dujowich; Eckert Seamans Cherin & Mellott, LLC

(57) ABSTRACT

Provided is an engineered antimicrobial peptide. Also provided is a composition comprising an engineered antimicrobial peptide. Provided is a method of treating a subject in need thereof, comprising administering a therapeutically effective amount of a composition comprising an engineered antimicrobial peptide. Also provided is a method of producing an engineered antimicrobial peptide.

10 Claims, 23 Drawing Sheets

Specification includes a Sequence Listing.

(56) References Cited

OTHER PUBLICATIONS

Conlon et al., Characterization of antimicrobial peptides in skin secretions from discrete populations of *Lithobates chiricahuensis* (Ranidae) from central and southern Arizona; Peptides; 32: 664-669. (Year: 2011).*
ABSS—Sequence Identity.pdf (Year: 2023).*
Bahar et al., Antimicrobial Peptides, Pharmaceuticals (2013), 6:1543-1575.
Bao et al., Modification Targeting the 'Rana Box' Motif of a Novel Nigrocin Peptide From Hylarana Latouchii Enhances and Broadens Its Potency Against Multiple Bacteria, Frontiers in Microbiology (Nov. 28, 2018), 9(2846):1-11.
Barksdale et al., Peptides from American Alligator Plasma Are Antimicrobial against Multi-Drug Resistant Bacterial Pathogens Including Acinetobacter Baumannii, BMC Microbiology (2016), 16(189):1-14.
Barksdale et al., Cathelicidin Antimicrobial Peptide from Alligator Mississippiensis Has Antibacterial Activity against Multi-Drug Resistant Acinetobacter Baumanii and Klebsiella Pneumoniae, Developmental & Comparative Immunology (May 2017), 70:135-144.
Browne et al., A New Era of Antibiotics: The Clinical Potential of Antimicrobial Peptides, International Journal of Molecular Sciences (2020), 21(7047):1-23.
Cardoso et al., Computer-Aided Design of Antimicrobial Peptides: Are We Generating Effective Drug Candidates?, Frontiers in Microbiology (Jan. 22, 2020), 10(3097):1-15.
Cepas et al., Relationship Between Biofilm Formation and Antimicrobial Resistance in Gram-Negative Bacteria, Microbial Drug Resistance (Jan. 2019), 25(1):72-79.
Chen et al., Simulation-Guided Rational de Novo Design of a Small Pore-Forming Antimicrobial Peptide, Journal of the American Chemical Society (2019), 141(12):4839-4848.
Wang et al., Large-Scale Analysis of Antimicrobial Activities in Relation to Amphipathicity and Charge Reveals Novel Characterization of Antimicrobial Peptides, Molecules (2017), 22(2037):1-8.
Methods for Dilution Antimicrobial Susceptibility Tests for Bacteria That Grow Aerobically; Approved Standard—Tenth Edition, Clinical and Laboratory Standards and Institute (Jan. 2015).
Conlon et al., Antimicrobial Peptides from the Skin Secretions of the New World Frogs *Lithobates capito* and *Lithobates warszewitschii* (Ranidae), Peptides (Oct. 2009), 30(10):1775-1781.
Dean et al., Natural and Synthetic Cathelicidin Peptides with Anti-Microbial and Anti-Biofilm Activity against *Staphylococcus aureus*, BMC Microbiology (2011), 11(114):1-12.
Gabere et al., Empirical Comparison of Web-Based Antimicrobial Peptide Prediction Tools, Bioinformatics (2017), 33(13):1921-1929.
Gautier et al., Heliquest: a web server to screen sequences with specific alpha-helical properties, Bioinformatics (Sep. 2008), 24(18):2101-2102.
Goraya et al., Ranatuerins: Antimicrobial Peptides Isolated from the Skin of the American Bullfrog, *Rana catesbeiana*, Biochemical and Biophysical Research Communications (Sep. 29, 1998), 250(3):589-592.
Henikoff et al., Amino Acid Substitution Matrices from Protein Blocks, Proceedings of the National Academy of Sciences of the United States of America (Nov. 1992), 89:10915-10919.
Hollmann et al., Antimicrobial Peptides: Interaction With Model and Biological Membranes and Synergism With Chemical Antibiotics, Frontiers in Chemistry (Jun. 5, 2018), 6(204):1-13.
Jahnsen et al., Characterization of a Proteolytically Stable Multifunctional Host Defense Peptidomimetic, Chemistry & Biology (Oct. 24, 2013), 20(10):1286-1295.
Jiang et al., "Specificity Determinants" Improve Therapeutic Indices of Two Antimicrobial Peptides Piscidin 1 and Dermaseptin S4 Against the Gram-Negative Pathogens Acinetobacter Baumannii and Pseudomonas Aeruginosa, Pharmaceuticals (2014), 7:366-391.

Joseph et al., ClassAMP: A Prediction Tool for Classification of Antimicrobial Peptides, IEEE/ACM Transactions on Computational Biology and Bioinformatics (2012), 9(5):1535-1538.
Kozic et al., Predicting the Minimal Inhibitory Concentration for Antimicrobial Peptides with Rana-Box Domain, Journal of Chemical Information and Modeling (2015), 55(10): 2275-2287.
Kyte et al., A Simple Method for Displaying the Hydropathic Character of a Protein, Journal of Molecular Biology (May 5, 1982), 157(1):105-132.
Lamiable et al., PEP-FOLD3: Faster de Novo Structure Prediction for Linear Peptides in Solution and in Complex, Nucleic Acids Research (2016), 44:W449-W454.
Lazzaro et al., Antimicrobial Peptides: Application Informed by Evolution, Science (May 1, 2020), 368(6490):1-20.
Lee et al., Design, Synthesis, and Antimicrobial Activities of Novel Functional Peptides against Gram-Positive and Gram-Negative Bacteria, Chemical Biology & Drug Design (May 6, 2019), 94(2):1537-1544.
Li et al., Discovery of Novel Caeridins from the Skin Secretion of the Australian White's Tree Frog, *Litoria caerulea*, International Journal of Genomics (Jul. 11, 2018), 2018(8158453):1-18.
Liu et al., Antibiotic Adjuvants: An Alternative Approach to Overcome Multi-Drug Resistant Gram-Negative Bacteria, Critical Reviews in Microbiology (2019), 45(3):301-314.
Mahlapuu et al., Antimicrobial Peptides: An Emerging Category of Therapeutic Agents, Frontiers in Cellular and Irifection Microbiology (Dec. 27, 2016), 6(194):1-12.
Marani et al., Characterization and Biological Activities of Ocellatin Peptides from the Skin Secretion of the Frog *Leptodactylus pustulatus*, Journal of Natural Products (2015), 78(7):1495-1504.
Mishra et al., Low Cationicity Is Important for Systemic in Vivo Efficacy of Database-Derived Peptides against Drug-Resistant Gram-Positive Pathogens, Proceedings of the National Academy of Sciences of the United States of America (Jul. 2, 2019), 116(27):13517-13522.
Mishra et al., Ab Initio Design of Potent Anti-MRSA Peptides Based on Database Filtering Technology, Journal of the American Chemical Society (Jul. 17, 2012), 134(30):12426-12429.
Mohanram et al., Salt-Resistant Short Antimicrobial Peptides, Peptide Science (May 2016), 106(3):345-356.
Okella et al., New Putative Antimicrobial Candidates: In Silico Design of Fish-Derived Antibacterial Peptide-Motifs, Frontiers in Bioengineering and Biotechnology (Dec. 3, 2020), 8(604041):1-10.
Osorio et al., Peptides: A Package for Data Mining of Antimicrobial Peptides, The R Journal (Jun. 2015), 7(1):4-14.
Otsuka, Yasunari. 2020. "Drug Discovery : Recent Progress and the Future Potent Antibiotics Active against Multidrug-Resistant Gram-Negative Bacteria" 68 (3): 182-90.
Pirtskhalava et al., DBAASP v3: Database of Antimicrobial/Cytotoxic Activity and Structure of Peptides as a Resource for Development of New Therapeutics, Nucleic Acids Research 49(DI):D288-D297, Nov. 5, 2020.
Sang et al., Identification and Target-Modifications of Temporin-PE: A Novel Antimicrobial Peptide in the Defensive Skin Secretions of the Edible Frog, *Pelophylax* KL *esculentus*, Biochemical and Biophysical Research Communications (Apr. 2019), 495(4):2539-2546.
Schwarz et al., Editorial: assessing the antimicrobial susceptibility of bacteria obtained from animals, J. Antimicrob. Chemother (2010), 65:601-604.
Silhavy et al., The Bacterial Cell Envelope, Cold Spring Harbor Perspectives in Biology (2010), 2(5):a000414-a000414.
Singh et al., Peptide Secondary Structure Prediction Using Evolutionary Information, Biochem Biophys Res Commun. (Jan. 22, 2018), 495(4):2539-2546.
Tajbakhsh et al., The antimicrobial potential of a new derivative of cathelicidin from Bungarus fasciatus against methicillin-resistant *Staphylococcus aureus*, Journal of Microbiology (2018), 56(2):128-137.
Tornesello et al., Antimicrobial Peptides as Anticancer Agents: Functional Properties and Biological Activities, Molecules (2020), 25(12):1-25.

(56) References Cited

OTHER PUBLICATIONS

Torrent et al., Towards the Rational Design of Antimicrobial Peptides: Recent Developments in Computational Tools, Science and Technology Against Microbial Pathogens (Jan. 2011).

Turner et al., Activities of LL-37, a cathelin-associated antimicrobial peptide of human neutrophils. Antimicrob. Agents Chemother. (Sep. 1998), 42(9):2206-2214.

Waghu et al., CAMPR3: A Database on Sequences, Structures and Signatures of Antimicrobial Peptides, Nucleic Acids Research (Jan. 4, 2016), 44(D1):D1094-D1097.

Wang et al., APD3: The Antimicrobial Peptide Database as a Tool for Research and Education, Nucleic Acids Research (Jan. 4, 2019), 44(D1):D1087-1093.

Wang et al., Identification and Functional Analyses of Novel Antioxidant Peptides and Antimicrobial Peptides from Skin Secretions of Four East Asian Frog Species, Acta Biochimica et Biophysica Sinica (Apr. 2017), 49(6):550-559.

Wang et al., Snake Cathelicidin from Bungarus Fasciatus Is a Potent Peptide Antibiotics, PLoS One (Sep. 16, 2008), 3(9):e3217:1-9.

Wieczorek et al., Structural Studies of a Peptide with Immune Modulating and Direct Antimicrobial Activity, Chemistry & Biology (2010), 17(9):970-980.

Wiegand et al., Agar and Broth Dilution Methods to Determine the Minimal Inhibitory Concentration (MIC) of Antimicrobial Substances, Nature Protocols (2008), 3(2):163-175.

Wimley et al., Experimentally Determined Hydrophobicity Scale for Proteins at Membrane Interfaces, Nature Structural Biology (1996), 3(10):842-848.

Yan et al., Deep-AmPEP30: Improve Short Antimicrobial Peptides Prediction with Deep Learning, Molecular Therapy. Nucleic Acids 20 (2020), 882-894.

\* cited by examiner

Calculated physicochemical properties of the synthetically designed peptides (PHNX -1 to -8)

| Name | Length (n) | Molecular Weight (Da) | Charge | Wimley-White whole-residue hydrophobicity (kcal/mol) | Boman index (kcal/mol) | GRAVY | APD3 defined hydro-phobic ratio (%) | Hydro-phobicity (H) | Hydro-phobic moment (μH) |
|---|---|---|---|---|---|---|---|---|---|
| PHNX-1 | 14 | 1640.20 | 4 | -0.6 | -1.5 | 1.46 | 71 | 0.51 | 0.41 |
| PHNX-2 | 13 | 1557.90 | 3 | -0.36 | -0.66 | 0.39 | 38 | 0.43 | 0.53 |
| PHNX-3 | 13 | 1369.72 | 4 | 0.63 | -0.32 | 0.66 | 38 | 0.35 | 0.50 |
| PHNX-4 | 13 | 1470.94 | 4 | -0.61 | -0.99 | 0.71 | 53 | 0.52 | 0.39 |
| PHNX-5 | 13 | 1369.72 | 4 | 1.13 | -0.22 | 0.17 | 38 | 0.37 | 0.34 |
| PHNX-6 | 13 | 1557.88 | 3 | -1.11 | 0.83 | 0.56 | 53 | 0.57 | 0.66 |
| PHNX-7 | 26 | 2512.06 | 6 | 0.85 | 0.46 | -0.22 | 44 | 0.47 | 0.65 |
| PHNX-8 | 26 | 2847.57 | 3 | 0.15 | 0.3 | 0.04 | 46 | 0.34 | 0.37 |

FIG. 8

Bioinformatics prediction of antimicrobial activity potential of peptides PHNX 1-8.

| Name | Predicted antimicrobial activity | | | | | | | | | |
|---|---|---|---|---|---|---|---|---|---|---|
| | AxPEP (Yan et al., 2020) | | CAMP$_{R3}$ (Waghu et al., 2016) | | | CLASSAMP (Joseph et al., 2012) | | | DBAASP (Pirtskhalava et al., 2021) |
| | Deep-AmPEP | RF-AmPEP | SVM | RF | ANN | DA | SVM | RF | |
| PHNX-1 | 0.92 | 0.97 | 0.99 | 0.98 | AMP | 1.00 | 0.98 | 0.99 | AMP |
| PHNX-2 | 0.73 | 0.93 | 0.94 | 0.54 | AMP | 0.99 | 0.99 | 0.95 | AMP |
| PHNX-3 | 0.77 | 0.95 | 0.98 | 0.73 | AMP | 1.00 | 0.99 | 0.97 | AMP |
| PHNX-4 | 0.93 | 0.99 | 0.99 | 0.99 | AMP | 1.00 | 0.98 | 0.99 | Non-AMP |
| PHNX-5 | 0.85 | 0.94 | 0.88 | 0.89 | AMP | 1.00 | 1.00 | 0.98 | Non-AMP |
| PHNX-6 | 0.86 | 0.70 | 0.85 | 0.97 | AMP | 0.85 | 0.99 | 0.95 | AMP |
| PHNX-7 | 0.92 | 0.84 | 1.00 | 1.00 | AMP | 1.00 | Not | 0.99 | AMP |
| PHNX-8 | 0.80 | 0.88 | 0.98 | 1.00 | AMP | 0.98 | Not | 0.94 | AMP |

*Not, not antibacterial*

FIG. 9

Minimum Inhibitory concentration (MIC) of PHNX peptides (μg/ml) against multi-drug resistant and antibiotic susceptible strains of *E. coli* and *S. aureus*.

| Bacteria peptides | *E. coli* ATCC 51659 | *S. aureus* ATCC 33592 | *E. coli* ATCC 4157 | *S. aureus* ATCC BAA-1718 | Consensus from predictors |
|---|---|---|---|---|---|
| PHNX-1 | 32 | 64 | 16 | 32 | Active (probability ≥ 0.92) |
| PHNX-2 | >100 | >100 | >100 | >100 | Mixed predictions (see text, 0.54 by CAMP$_{R3}$-RF) |
| PHNX-3 | >100 | >100 | >100 | >100 | Mixed predictions (see text, 0.73 by CAMP$_{R3}$-RF) |
| PHNX-4 | >100 | >100 | >100 | >100 | Active (except by DBAASP) |
| PHNX-5 | >100 | >100 | >100 | >100 | Active (except by DBAASP) |
| PHNX-6 | >100 | >100 | >100 | >100 | Mixed predictions (0.70 RF-AmPEP) |
| PHNX-7 | >64 | >100 | >100 | >100 | Active (except by CLASSAMP-SVM) |
| PHNX-8 | 64 | >64 | 32 | >100 | Active (except by CLASSAMP-SVM) |
| LL-37 | 32 | 64 | NT | NT | |
| BF-CATH | 8 | 64 | 4 | NT | |
| IDR-1018 | 16 | 16 | NT | 16 | |

FIG. 10

Half maximal effective concentration (EC$_{50}$) of PHNX peptides against multi-drug resistant strains of E. coli and S. aureus.

| Peptides | Bacteria | EC$_{50}$ (µg/ml) | 95% CI (µg/ml) | EC$_{50}$ (µM) | Consensus from predictors |
|---|---|---|---|---|---|
| PHNX-1 | E. coli ATCC 51659 | 0.12 | 0.06–0.3 | 0.06 | Active (probability ≥ 0.92) |
|  | S. aureus ATCC 25592 | 0.22 | 0.10–0.52 | 0.14 |  |
| PHNX-2 | E. coli ATCC 51659 | >10 | NA | >7.78 | Mixed predictions (see text, 0.54 by CAMP$_{R3}$-RF) |
|  | S. aureus ATCC 25592 | >10 | NA | >7.79 |  |
| PHNX-3 | E. coli ATCC 51659 | >10 | NA | >7.24 | Mixed predictions (see text, 0.70 by CAMP$_{R3}$-RF) |
|  | S. aureus ATCC 25592 | >10 | NA | >7.24 |  |
| PHNX-4 | E. coli ATCC 51659 | 2.91 | 1.30–6.53 | 1.96 | Active (except by DBAASP) |
|  | S. aureus ATCC 25592 | 4.85 | 1.90–12.36 | 3.29 |  |
| PHNX-5 | E. coli ATCC 51659 | 4.85 | 1.90–12.91 | 3.64 | Active (except by DBAASP) |
|  | S. aureus ATCC 25592 | >10 | NA | >7.86 |  |
| PHNX-6 | E. coli ATCC 51659 | 2.60 | 0.90–7.57 | 1.72 | Mixed predictions (0.70 RF-AmmEP) |
|  | S. aureus ATCC 25592 | 7.94 | 2.86–22.13 | 5.24 |  |
| PHNX-7 | E. coli ATCC 51659 | 0.04 | 0.02–0.12 | 0.03 | Active (except by CLASSAMP-SVM) |
|  | S. aureus ATCC 25592 | 2.09 | 0.61–7.10 | 0.83 |  |
| PHNX-8 | E. coli ATCC 51659 | 0.08 | 0.02–0.14 | 0.02 | Active (except by CLASSAMP-SVM) |
|  | S. aureus ATCC 25592 | 3.31 | 0.89–12.29 | 1.12 |  |

NA refers to not applicable where the 95% Confidence interval could not be calculated. IDR-1018 was used as a control against E. coli and S. aureus and demonstrated bacterial killing at 100 µg/ml.

ANTIMICROBIAL PEPTIDES AND RELATED METHODS

CROSS-REFERENCE TO RELATED APPLICATIONS

The instant application is entitled to priority under 35 U.S.C. § 119(e) to U.S. Provisional Application No. 63/236,805, filed Aug. 25, 2021, which is hereby incorporated by reference in its entirety.

FIELD

The general inventive concepts relate to the field of antimicrobial peptides, their uses, and methods for designing antimicrobial peptides.

SEQUENCE LISTING

The content of the electronic sequence listing (306564-00034_Sequence_Listing.xml; Size: 12,026 bytes; and Date of Creation: Aug. 25, 2022) is herein incorporated by reference in its entirety.

BACKGROUND

Antimicrobial peptides (AMPs) are evolutionarily conserved, small, cationic, amphiphilic molecules produced by prokaryotes and eukaryotes with antimicrobial and immunomodulatory properties (Lazzaro, Zasloff, and Rolff 2020; Tornesello et al. 2020). AMPs are typically less than 50 amino acids in length, contain on average 41% hydrophobic residues and target the bacterial membrane enabling a fast mechanism of action preventing the organism from developing resistance (Browne et al. 2020). Overuse of antibiotics has led to a crisis due to the emergence of antibiotic-resistant bacteria. As we approach a post-antibiotic era, AMPs present therapeutic potential due to their proven broad-spectrum activity and characteristics that set them apart from traditional antibiotics (Browne et al. 2020; Cardoso et al. 2020).

Gram-negative bacteria have key structural differences from gram-positive bacteria that make them intrinsically harder to eradicate. Gram-negative bacteria contain an outer membrane that protects the bacterium from environmental toxins and provides efflux out of the cell (Silhavy, Kahne, and Walker 2010). This membrane permeability barrier has historically restricted the discovery of narrow-spectrum antibiotics against gram-negative bacteria and this challenge is further compounded due to the rise in multi-drug resistance (MDR) strains resistant to multiple classes of antibiotics (Liu et al. 2019; Otsuka 2020). Finally, gram-negative bacteria can also use biofilms (a virulence factor) as a means to confer phenotypic antibiotic resistance which can make the bacteria up to 1000-fold times more resistant when embedded in the exopolysaccharide matrix (Cepas et al. 2018). Thus, novel antimicrobials are needed to combat multi-drug resistant gram-negative bacterial infections to decrease morbidity and mortality from these infections.

Computational approaches such as in silico machine-learning algorithm assisted motif identification using physiochemical properties (Okella et al. 2020), de novo design (Chen et al. 2019), rational ab initio design (Mishra and Wang 2012), redesigning and optimizing existing AMPs (Torrent et al. 2011), quantitative structure-activity relationship (QSAR) computational modeling and screening (Cardoso et al. 2020) have been used to design AMPs; however, few synthetic AMPs have reached clinical therapeutic potential. Computational tools can be leveraged not only to design but also to predict AMP's function as AMP discovery and testing in vitro can be time consuming as well as expensive.

There remains a need for improved antimicrobial peptides and methods of producing antimicrobial peptides, as well as methods of treatment comprising administration of antimicrobial peptides.

SUMMARY

Provided is an engineered antimicrobial peptide (AMP) comprising an amino acid sequence selected from the group consisting of:
  FLLKIVALLKKKLL (SEQ ID NO:1) or an antimicrobial peptide having at least 70%, 80%, 90%, 91%, 92%, 93%, 94%, 95%, 96%, 97%, 98%, or 99% amino sequence identity thereto,
  FGKLLKLGKGLGG (SEQ ID NO:2) or an antimicrobial peptide having at least 70%, 80%, 90%, 91%, 92%, 93%, 94%, 95%, 96%, 97%, 98%, or 99% amino sequence identity thereto,
  FGKLLKLGKGLKG (SEQ ID NO:3) or an antimicrobial peptide having at least 70%, 80%, 90%, 91%, 92%, 93%, 94%, 95%, 96%, 97%, 98%, or 99% amino sequence identity thereto,
  FLLKLGLGKKKLL (SEQ ID NO:4) or an antimicrobial peptide having at least 70%, 80%, 90%, 91%, 92%, 93%, 94%, 95%, 96%, 97%, 98%, or 99% amino sequence identity thereto,
  FLIKILKGGKGGK (SEQ ID NO:5) or an antimicrobial peptide having at least 70%, 80%, 90%, 91%, 92%, 93%, 94%, 95%, 96%, 97%, 98%, or 99% amino sequence identity thereto,
  FIGAIASYLKKFR (SEQ ID NO:6) or an antimicrobial peptide having at least 70%, 80%, 90%, 91%, 92%, 93%, 94%, 95%, 96%, 97%, 98%, or 99% amino sequence identity thereto,
  GVVDIIKGAGKKFAKGLAGKIANKK (SEQ ID NO:7) or an antimicrobial peptide having at least 70%, 80%, 90%, 91%, 92%, 93%, 94%, 95%, 96%, 97%, 98%, or 99% amino sequence identity thereto, and
  GLMDTVKNAAKNLAGQLLDKIKCKITGC (SEQ ID NO:8) or an antimicrobial peptide having at least 70%, 80%, 90%, 91%, 92%, 93%, 94%, 95%, 96%, 97%, 98%, or 99% amino sequence identity thereto.

In some embodiments, the antimicrobial peptide has antimicrobial activity against gram-negative bacteria. In further embodiments, the gram-negative bacteria is *E. coli* 4157, or *E. coli* O157:H7 51659. In some embodiments, the antimicrobial peptide has antimicrobial activity against gram-positive bacteria. In further embodiments, the gram-positive bacteria is *S. aureus* BAA-1718, or *S. aureus* MRSA 33592. In further embodiments, the antimicrobial peptide has antimicrobial activity against both gram-negative and gram-positive bacteria.

Provided is a composition comprising at least one antimicrobial peptide, optionally comprising a pharmaceutically acceptable carrier.

Provided is a method of killing or controlling growth of a microorganism comprising administering a therapeutically effective amount of the composition of any one of the previous embodiments.

Provided is a method of treating a subject in need thereof, comprising administering a therapeutically effective amount of the composition of any one of the previous embodiments.

Provided is a method of disinfecting a surface of an article comprising applying to the surface an effective amount of the composition of any one of the previous embodiments.

Provided is a disinfecting solution comprising at least one antimicrobial peptide of any one of the previous embodiments and optionally an acceptable carrier.

Provided is a method of producing an engineered antimicrobial peptide comprising:
providing an antimicrobial peptide (AMP) dataset;
selecting AMPs from said dataset by length; and
calculating an amino acid occurring most frequently per position in each selected AMP.

In some embodiments, the AMP dataset comprises AMPs with activity against gram-negative and gram-positive bacteria. In some embodiments, the AMP dataset comprises AMPs with activity against gram-negative bacteria irrespective of their activity against gram-positive bacteria. In some embodiments, the AMP dataset comprises AMPs with activity against only gram-negative bacteria. In some embodiments, the AMP dataset comprises AMPs with activity against only gram-positive bacteria.

In some embodiments, the AMPs are selected by length by selecting AMPs that have the most frequent lengths in the dataset.

In some embodiments, the AMPs are selected by length by selecting AMPs that are about 12 to about 28 residues in length. In further embodiments, the AMPs are selected by length by selecting AMPs that are 12, 13, 14, 15, 16, 17, 18, 19, 20, 21, 22, 23, 24, 25, 26, 27, or 28 residues in length, or combinations thereof.

In some embodiments, to determine the amino acid per position, the Excel formula MID($B2, COLUMNS($B$2:C$2), position number) is used followed by COUNTIF ($D$2:$D$16, B19) to count the frequency of each residue per position. In some embodiments, the formula MAX is used to calculate a residue that occurs most frequently per position.

In some embodiments, the method further comprises engineering an antimicrobial peptide that comprises in each position the amino acid occurring most frequently per position in the dataset.

In some embodiments, the method further comprises conducting bioinformatics prediction of antibacterial activity of the engineered AMP.

In some embodiments, engineered AMPs are designed to have 5 and 6 hydrophobic residues for 13- and 14-residue long AMPs respectively.

In some embodiments, engineered AMPs are designed to have a charge of about +3 (C3) to about +6 (C6). In further embodiments, engineered AMPs are designed to have a charge of +4 (C4).

In some embodiments, engineered AMPs are designed comprising the sequence:
FXXKXXKGGKGGK (SEQ ID NO: 11), wherein X in position 2 is isoleucine or leucine, X in position 3 is isoleucine or leucine, X in position 5 is isoleucine or leucine, and X in position 6 is isoleucine or leucine.

Provided is an engineered antimicrobial peptide produced by the method of any one of the preceding embodiments.

In some embodiments, the engineered antimicrobial peptide is synthetic.

In some embodiments, the engineered antimicrobial peptide is not naturally occurring.

Provided is a composition comprising at least one engineered antimicrobial peptide of any one of the preceding embodiments, optionally comprising a pharmaceutically acceptable carrier.

Provided is a method of killing or controlling growth of a microorganism comprising administering a therapeutically effective amount of the composition of any one of the preceding embodiments.

Provided is a method of treating a subject in need thereof, comprising administering a therapeutically effective amount of the composition of any one of the preceding embodiments.

Provided is a method of disinfecting a surface of an article comprising applying to the surface an effective amount of the composition of any one of the preceding embodiments.

Also provided is a disinfecting solution comprising at least one antimicrobial peptide of any one of the preceding embodiments and optionally an acceptable carrier.

DESCRIPTION OF THE FIGURES

FIG. 2A: lengths of AMPs in Dataset 1. FIG. 2B: Frequency of total amino acid residues in Dataset 1. FIG. 2C: Change of the AMPs in Dataset 1. FIG. 2D: Hydrophobicity percentage of AMPs in Dataset 1 (hydrophobicity was calculated as a percentage of hydrophobic amino acids, based on the Kyte and Doolittle scale (Kyte and Doolittle 1982) divided by the total number of amino acids per AMP).

FIG. 3A: Antibiotic susceptible $E.$ $coli$ 4157. FIG. 3B: Antibiotic resistant $E.$ $coli$ O157:H7 51659. FIG. 3C: $S.$ $aureus$ BAA-1718. FIG. 3D: $S.$ $aureus$ MRSA 33592. PHNX-1 led to almost 0% bacterial survival against all strains and PHNX-7 and PHNX-8 against the Gram-negative bacteria ($E.$ $coli$ 4157 and $E.$ $coli$ O157:H7 51659).

FIG. 4A: Antibiotic susceptible $E.$ $coli$ 4157. FIG. 4B: $E.$ $coli$ O157:H7 51659 (MIC=32 µg/ml). FIG. 4C: $S.$ $aureus$ BAA-1718 (MIC=32 µg/ml). FIG. 4D: $S.$ $aureus$ 33592 (MIC=64 µg/ml).

FIG. 5A: PHNX-1. FIG. 5B: PHNX-6. FIG. 5C: PHNX-7. FIG. 5D: PHNX-8.

FIG. 7A: lengths of AMPs in Dataset2. FIG. 7B: frequency of total amino acid residues in Dataset 2. FIG. 7C: charge of the AMPs in Dataset2. FIG. 7D: hydrophobicity percentage of AMPs in Dataset2. Hydrophobicity was calculated as a percentage of hydrophobic amino acids, based on the Kyte and Doolittle scale (Kyte and Doolittle, 1982) divided by the total number of amino acids per AMP.

FIG. 8 shows a table of the calculated physicochemical properties of the synthetically designed peptides (PHNX-1 to PHNX-8).

FIG. 9 shows a table of the bioinformatics prediction of antimicrobial activity potential of peptides PHNX-1-8.

FIG. 10 shows a table of the minimum inhibitory concentration (MIC) of PHNX peptides (μg/ml) against multi-drug resistant and antibiotic susceptible strains of *E. coli* and *S. aureus*. NT refers to not tested. LL-37, BF-CATH, and IDR-1018 were control peptides tested against the bacterial strains. The consensus from predictors of FIG. 9 is indicated in the last column for comparison.

FIG. 11 shows a table of the half maximal effective concentration ($EC_{50}$) of PHNX peptides against multi-drug resistant strains of *E. coli* and *S. aureus*.

Figure 12B:
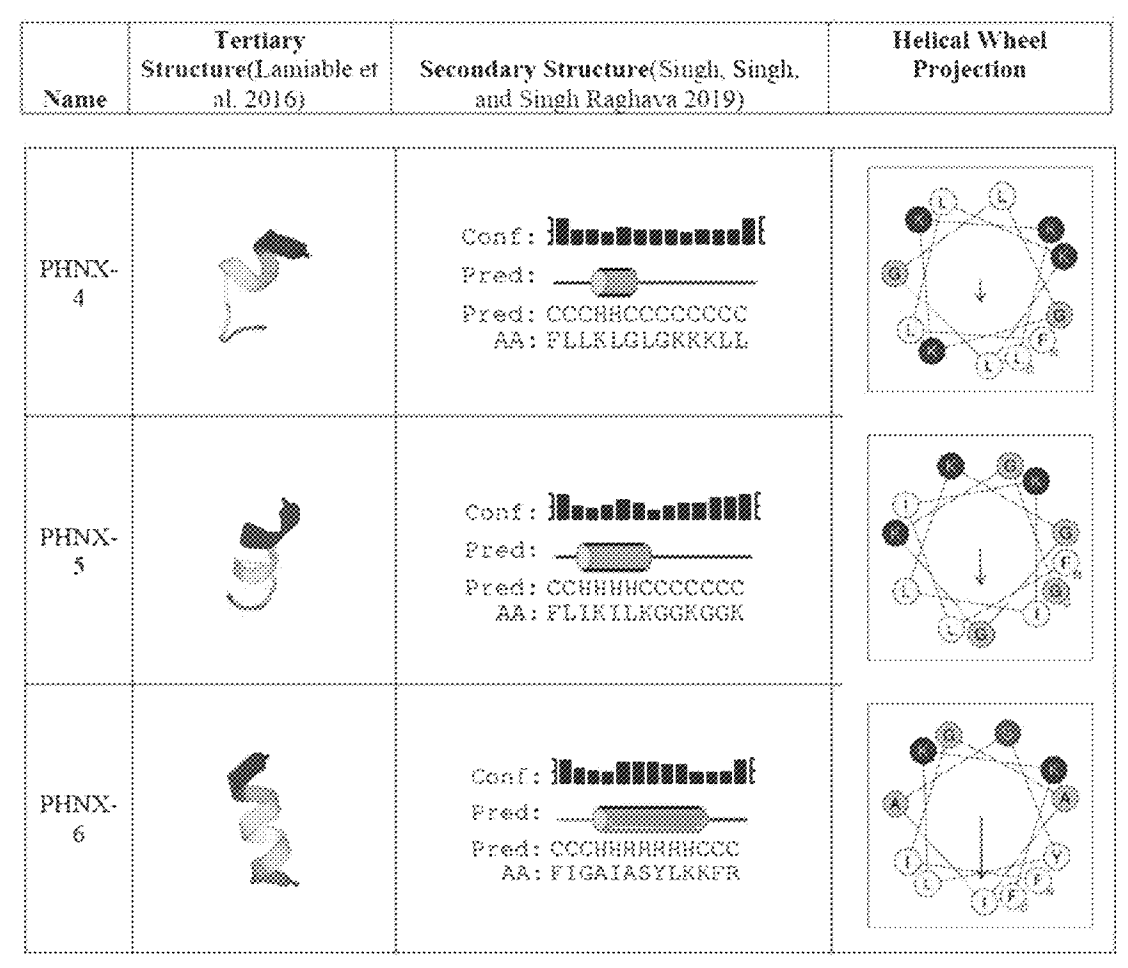

FIGS. 12A-12C show secondary (predicted C=coil and H=helix) and tertiary structures of the designed synthetic AMPs. FIG. 12A shows PHNX-1 (SEQ ID NO: 1), PHNX-2 (SEQ ID NO: 2) and PHNX-3 (SEQ ID NO: 3). FIG. 12B shows PHNX-4 (SEQ ID NO: 4), PHNX-5 (SEQ ID NO: 5) and PHNX-6 (SEQ ID NO: 6). FIG. 12C shows PHNX-7 (SEQ ID NO: 7) and PHNX-8 (SEQ ID NO: 8).

DETAILED DESCRIPTION

Figure 1:
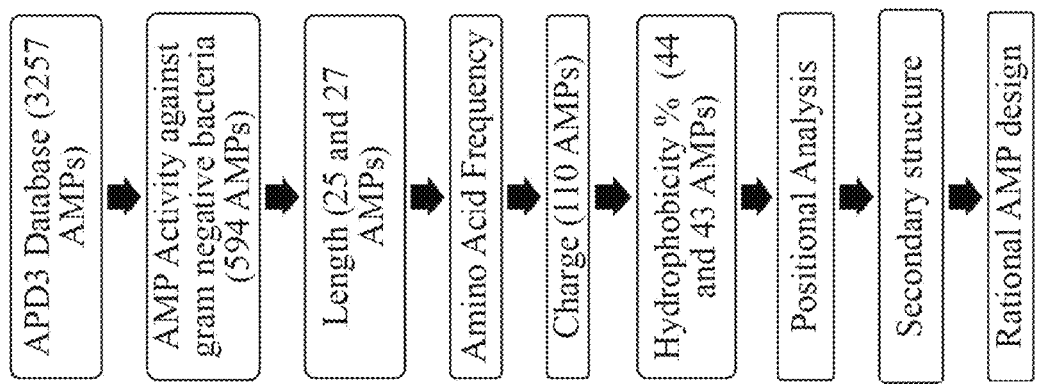
FIG. 1 shows a flowchart describing the ab initio rational AMP design process for Dataset 1 including an additional filter: positional analysis.

While the general inventive concepts are susceptible of embodiment in many forms, there are shown in the drawings, and will be described herein in detail, specific embodiments thereof with the understanding that the present disclosure is to be considered an exemplification of the principles of the general inventive concepts. Accordingly, the general inventive concepts are not intended to be limited to the specific embodiments illustrated herein.

It is also to be understood that the terminology used herein is for the purpose of describing particular embodiments only, and is not intended to be limiting.

The articles "a" and "an" are used herein to refer to one or more than one (i.e., to at least one) of the grammatical object of the article. By way of example, "a cell" means one cell or more than one cell.

"About" as used herein when referring to a measurable value such as an amount, a temporal duration, and the like, is meant to encompass variations of ±5%, preferably ±1%, and still more preferably ±0.1% from the specified value, as such variations are appropriate to perform the disclosed methods.

Embodiments described herein as "comprising" one or more features may also be considered as disclosure of the corresponding embodiments "consisting of" and/or "consisting essentially of" such features.

As used herein a "therapeutically effective amount" refers to an amount that is sufficient to ameliorate the state of the subject so treated.

As used herein "ameliorate" means a lessening of the detrimental effect of a disease, disorder or condition in a subject receiving treatment.

Antimicrobial peptides (AMPs) are ubiquitous amongst living organisms and are part of the innate immune system with the ability to kill pathogens directly or indirectly by modulating the immune system. AMPs have potential as a novel therapeutic against bacteria due to their quick-acting mechanism of action that prevents bacteria from developing resistance. Additionally, there is a dire need for therapeutics with activity specifically against gram-negative bacterial infections that are intrinsically difficult to treat, with or without acquired drug resistance. Development of new antibiotics has slowed in recent years and novel therapeutics (like AMPs) with a focus against gram-negative bacteria are needed. Novel AMPs were designed by the methods described herein, termed PHNX peptides, using ab initio computational design (database filtering technology combined with the novel positional analysis on APD3 dataset of AMPs with activity against gram-negative bacteria) and their theoretical function was assessed using machine learning algorithms, and their activity was validated experimentally. These AMPs were tested to establish their minimum inhibitory concentration (MIC) and half-maximal bactericidal concentration ($EC_{50}$) under Clinical and Laboratory Standards and Institute (CLSI) methodology against antibiotic resistant and antibiotic susceptible *Escherichia coli* and MRSA (Methicillin Resistant *Staphylococcus aureus*) bacteria. Laboratory-based experimental results were compared to computationally predicted activities for each of the peptides to ascertain the accuracy of the computational tools used. The AMPs were then evaluated for cytotoxicity using hemolysis against human red blood cells. Several PHNX AMPs demonstrated good MIC and $EC_{50}$ activity and thus present novel synthetic peptides with a potential for therapeutic use.

Due to the lack of new antimicrobials being developed to combat gram-negative infections, computational approaches combined with traditional laboratory benchtop assays were used to develop and assess novel AMPs against drug resistant and antibiotic susceptible strains of gram-negative bacteria. The ab initio database filtering technology (DFT) method combined with positional analysis was used on two datasets obtained from APD3 (aps.unmc.edu), which resulted in the design of novel, synthetic AMPs.

Synthetic AMPs developed using computational methods pose potential as a novel antimicrobial therapeutic which can be used as a drug to treat infections caused by antibiotic resistant and susceptible bacteria. AMPs can also be used commercially synergistically with traditional antibiotics, conjugated with polymers on medical devices and developed as a topical applicator to treat infected wounds.

Antimicrobial Peptides

Provided is an engineered antimicrobial peptide (AMP) comprising an amino acid sequence selected from the group consisting of:

FLLKIVALLKKKLL (SEQ ID NO:1) or an antimicrobial peptide having at least 70%, 80%, 90%, 91%, 92%, 93%, 94%, 95%, 96%, 97%, 98%, or 99% amino sequence identity thereto, FGKLLKLGKGLGG (SEQ ID NO:2) or an antimicrobial peptide having at least 70%, 80%, 90%, 91%, 92%, 93%, 94%, 95%, 96%, 97%, 98%, or 99% amino sequence identity thereto, FGKLLKLGKGLKG (SEQ ID NO:3) or an antimicrobial peptide having at least 70%, 80%, 90%, 91%, 92%, 93%, 94%, 95%, 96%, 97%, 98%, or 99% amino sequence identity thereto, FLLKLGLGKKKLL (SEQ ID NO:4) or an antimicrobial peptide having at least 70%, 80%, 90%, 91%, 92%, 93%, 94%, 95%, 96%, 97%, 98%, or 99% amino sequence identity thereto, FLIKILKGGKGGK (SEQ ID NO:5) or an antimicrobial peptide having at least 70%, 80%, 90%, 91%, 92%, 93%, 94%, 95%, 96%, 97%, 98%, or 99% amino sequence identity thereto, FIGAIASYLKKFR (SEQ ID NO:6) or an antimicrobial peptide having at least 70%, 80%, 90%, 91%, 92%, 93%, 94%, 95%, 96%, 97%, 98%, or 99% amino sequence identity thereto, GVVDIIKGAGKKFAKGLAGKIANKK (SEQ ID NO:7) or an antimicrobial peptide having at least 70%, 80%, 90%, 91%, 92%, 93%, 94%, 95%, 96%, 97%, 98%, or 99% amino sequence identity thereto, and GLMDTVKNAAKNLAGQLLDKIKCKITGC (SEQ ID NO:8) or an antimicrobial peptide having at least 70%, 80%, 90%, 91%, 92%, 93%, 94%, 95%, 96%, 97%, 98%, or 99% amino sequence identity thereto.

Also provided is an engineered AMP comprising SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, comprising a substitution of at least one amino acid residue. In some embodiments, the substitution is of 1, 2, 3, 4, 5, or 6 amino acid residues. In some embodiments, the substitution is a conservative substitution. In some embodiments, the substitution is of one hydrophilic amino acid for another hydrophilic amino acid. In some embodiments, the substitution is of one hydrophobic amino acid for another hydrophobic amino acid. In some embodiments, the substitution replaces an L-amino acid with a D-amino acid of the same identity. In some embodiments, the substitution replaces an D-amino acid with a L-amino acid of the same identity.

Also provided is an engineered AMP comprising SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, comprising a truncation of at least one amino acid residue at the N-terminus, C-terminus, or both.

In some embodiments, the antimicrobial peptide has antimicrobial activity against gram-negative bacteria. In further embodiments, the gram-negative bacteria is *E. coli* 4157, or *E. coli* O157:H7 51659. In some embodiments, the antimicrobial peptide has antimicrobial activity against gram-positive bacteria. In further embodiments, the gram-positive bacteria is *S. aureus* BAA-1718, or *S. aureus* MRSA 33592. In further embodiments, the antimicrobial peptide has antimicrobial activity against both gram-negative and gram-positive bacteria.

In some embodiments, the antimicrobial peptide has antimicrobial activity against bacteria of the genera *Staphylococcus, Escherichia, Kebsiella, Pseudomonas, Serratia, Proteus, Enterobacter, Streptococcus,* or *Acinetobacter*. In some embodiments, the *Staphylococcus* is *S. aureus*. In some embodiments, the *Klebsiella* is *K. pneumoniae*. In some embodiments, the *Pseudomonas* is *P. aeruginosa*. In some embodiments, the *Serratia* is *S. marcescens*. In some embodiments, the *Proteus* is *Proteus mirabilis*. In some embodiments, the *Enterobacter* is *Enterobacter cloacae*. In some embodiments, the *Streptococcus* is *Streptococcus pneumoniae*. In some embodiments, the *Acinetobacter* is *A. baumannii* or *A. johnonii*.

In further embodiments, the antimicrobial peptide has antimicrobial activity against bacteria of the genera *Staphylococcus* and/or *Escherichia*.

In some embodiments, the antimicrobial peptide has antimicrobial activity against fungi. In further embodiments, the antimicrobial peptide has antimicrobial activity against *Candida*. In some embodiments, the *Candida* is *C. albicans, C. glabrata, C. parapsilosis,* or *C. quillermonidae*. In some embodiments, the antimicrobial peptide has antimicrobial activity against bacteria and fungi.

In some embodiments, the antimicrobial peptide is conjugated to another molecule. In some embodiments, the other molecule is an antibody, ligand, receptor, or other binding molecule. In further embodiments, the other molecule binds to a target cell.

Provided is a composition comprising at least one antimicrobial peptide, optionally comprising a pharmaceutically acceptable carrier. In some embodiments, the pharmaceutically acceptable carrier is aqueous or nonaqueous. In some embodiments, the pharmaceutically acceptable carrier is sterile. The pharmaceutically acceptable may be a solution, suspension or emulsion. The aqueous carrier may include water, saline, or buffered solutions. The nonaqueous carrier may include propylene glycol, polyethylene glycol, or a vegetable oil.

In some embodiments, the composition further comprises a drug, for example an antibiotic.

Provided is a method of killing or controlling growth of a microorganism comprising administering a therapeutically effective amount of the composition of any one of the previous embodiments.

Provided is a method of treating a subject in need thereof, comprising administering a therapeutically effective amount of the composition of any one of the previous embodiments. In some embodiments, the subject is further treated with a drug, for example an antibiotic.

Provided is a method of disinfecting a surface of an article comprising applying to the surface an effective amount of the composition of any one of the previous embodiments.

Provided is a disinfecting solution comprising at least one antimicrobial peptide of any one of the previous embodiments and optionally an acceptable carrier. In some embodiments, the disinfecting solution further comprises a detergent.

Provided is a medical instrument, catheter, or substance or material, which is coated with at least one antimicrobial peptide of any one of the previous embodiments.

Methods

Provided is a method of producing an engineered antimicrobial peptide comprising:
  providing an antimicrobial peptide (AMP) dataset;
  selecting AMPs from said dataset by length; and
  calculating an amino acid occurring most frequently per position in each selected AMP.

In some embodiments, the AMP dataset comprises AMPs with activity against gram-negative and gram-positive bacteria. In some embodiments, the AMP dataset comprises AMPs with activity against gram-negative bacteria irrespective of their activity against gram-positive bacteria. In some embodiments, the AMP dataset comprises AMPs with activity against only gram-negative bacteria. In some embodiments, the AMP dataset comprises AMPs with activity against only gram-positive bacteria.

In some embodiments, the AMPs are selected by length by selecting AMPs that have the most frequent lengths in the dataset.

In some embodiments, the AMPs are selected by length by selecting AMPs that are about 12 to about 28 residues in length. In further embodiments, the AMPs are selected by length by selecting AMPs that are 12, 13, 14, 15, 16, 17, 18, 19, 20, 21, 22, 23, 24, 25, 26, 27, or 28 residues in length, or combinations thereof.

In some embodiments, to determine the amino acid per position, the Excel formula MID($B2, COLUMNS($B$2:C$2), position number) is used followed by COUNTIF ($D$2:$D$16, B19) to count the frequency of each residue per position. In some embodiments, the formula MAX is used to calculate a residue that occurs most frequently per position.

In some embodiments, the method further comprises engineering an antimicrobial peptide that comprises in each position the amino acid occurring most frequently per position in the dataset.

In some embodiments, the method further comprises conducting bioinformatics prediction of antibacterial activity of the engineered AMP.

In some embodiments, engineered AMPs are designed to have 5 and 6 hydrophobic residues for 13- and 14-residue long AMPs respectively.

In some embodiments, engineered AMPs are designed to have a charge of about +3 (C3) to about +6 (C6). In further embodiments, engineered AMPs are designed to have a charge of +3 (C3), +4 (C4), +5 (C5), or +6 (C6). In further embodiments, engineered AMPs are designed to have a charge of +4 (C4).

In some embodiments, engineered AMPs are designed comprising the sequence:

FXXKXXKGGKGGK (SEQ ID NO: 11), wherein X in position 2 is isoleucine or leucine, X in position 3 is isoleucine or leucine, X in position 5 is isoleucine or leucine, and X in position 6 is isoleucine or leucine.

Provided is an engineered antimicrobial peptide produced by the method of any one of the preceding embodiments.

In some embodiments, the engineered antimicrobial peptide is synthetic.

In some embodiments, the engineered antimicrobial peptide is not naturally occurring.

In some embodiments, the antimicrobial peptide has antimicrobial activity against bacteria of the genera *Staphylococcus, Escherichia, Kebsiella, Pseudomonas, Serratia, Proteus, Enterobacter, Streptococcus*, or *Acinetobacter*. In some embodiments, the *Staphylococcus* is *S. aureus*. In some embodiments, the *Klebsiella* is *K. pneumoniae*. In some embodiments, the *Pseudomonas* is *P. aeruginosa*. In some embodiments, the *Serratia* is *S. marcescens*. In some embodiments, the *Proteus* is *Proteus mirabilis*. In some embodiments, the *Enterobacter* is *Enterobacter cloacae*. In some embodiments, the *Streptococcus* is *Streptococcus pneumoniae*. In some embodiments, the *Acinetobacter* is *A. baumannii* or *A. johnonii*.

In further embodiments, the antimicrobial peptide has antimicrobial activity against bacteria of the genera *Staphylococcus* and/or *Escherichia*.

In some embodiments, the antimicrobial peptide has antimicrobial activity against fungi. In further embodiments, the antimicrobial peptide has antimicrobial activity against *Candida*. In some embodiments, the *Candida* is *C. albicans, C. glabrata, C. parapsilosis*, or *C. quillermonidae*. In some embodiments, the antimicrobial peptide has antimicrobial activity against bacteria and fungi.

Provided is a composition comprising at least one engineered antimicrobial peptide of any one of the preceding embodiments, optionally comprising a pharmaceutically acceptable carrier. In some embodiments, the pharmaceutically acceptable carrier is aqueous or nonaqueous. In some embodiments, the pharmaceutically acceptable carrier is sterile. The pharmaceutically acceptable may be a solution, suspension or emulsion. The aqueous carrier may include water, saline, or buffered solutions. The nonaqueous carrier may include propylene glycol, polyethylene glycol, or a vegetable oil.

Provided is a method of killing or controlling growth of a microorganism comprising administering a therapeutically effective amount of the composition of any one of the preceding embodiments.

Provided is a method of treating a subject in need thereof, comprising administering a therapeutically effective amount of the composition of any one of the preceding embodiments.

Provided is a method of disinfecting a surface of an article comprising applying to the surface an effective amount of the composition of any one of the preceding embodiments.

Also provided is a disinfecting solution comprising at least one antimicrobial peptide of any one of the preceding embodiments and optionally an acceptable carrier. In some embodiments, the disinfecting solution further comprises a detergent.

The following examples are not intended to be limiting.

EXAMPLES

Materials and Methods
Antimicrobial Peptides Design

Ab initio database filtering technology (DFT) was used as the first step to design novel AMPs (Mishra and Wang, 2012). The database ADP3 was used to obtain two AMP datasets (Wang et al., 2016). Dataset 1 (594 AMPs) included AMPs with reported activity against Gram-negative bacteria irrespective of their reported activity against Gram-positive bacteria. Dataset 2 (299 AMPs) included AMPs with reported activity against only Gram-negative bacteria. R-Studio (Package "Peptides") and Microsoft Excel was used to obtain the properties of the AMPs dataset obtained from APD3. FIG. 1 illustrates the ab initio database filtering technology method used, where analyzing existing AMP properties is used to filter AMPs followed by rationally designing synthetic AMPs that meet the filtered criteria.

PHNX-2 Through PHNX-5

Figure 2A:
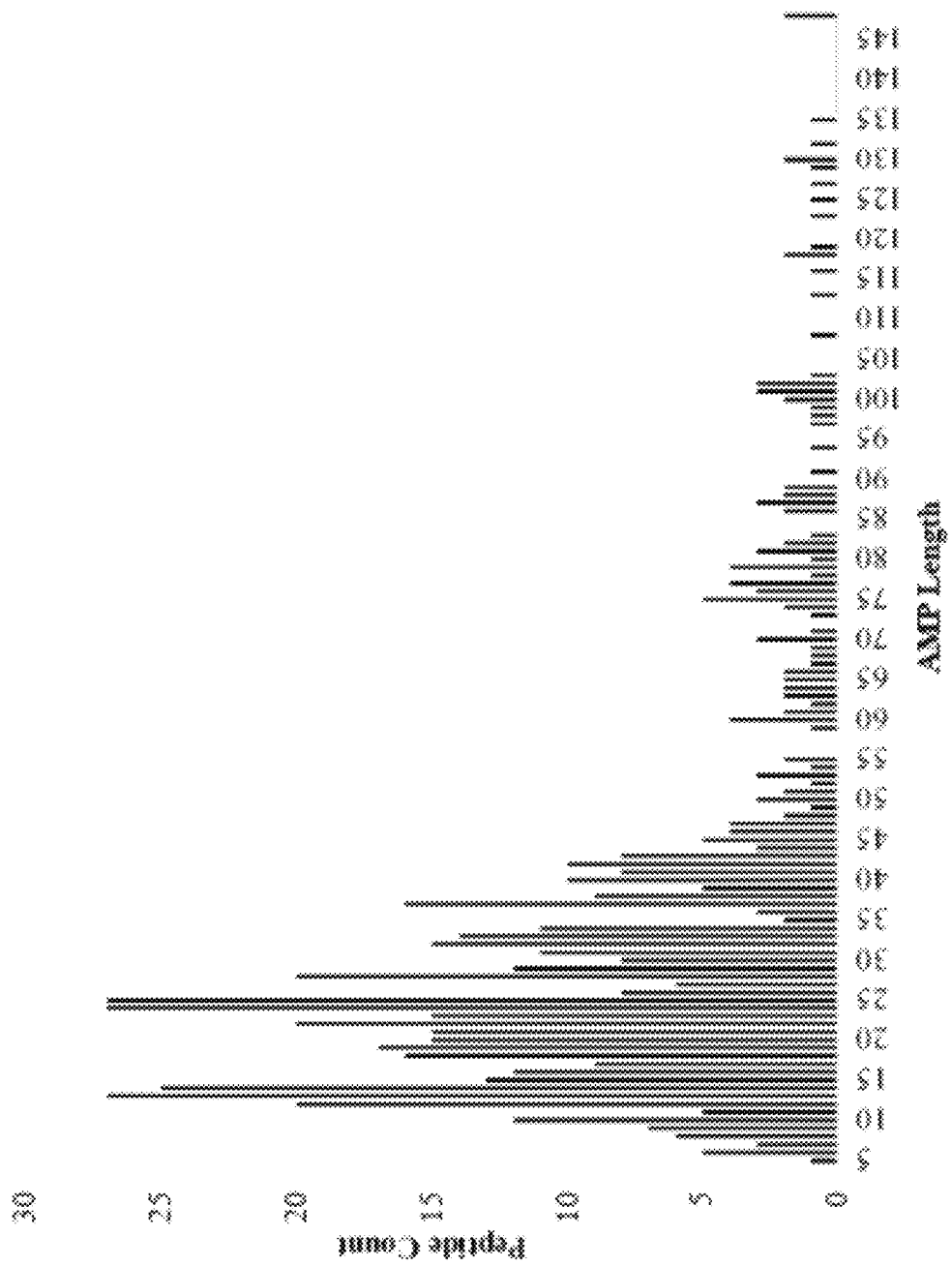
FIGS. 2A-2D show statistics of AMP properties obtained from antimicrobial peptide database 3 (APD3).
Figure 2B:
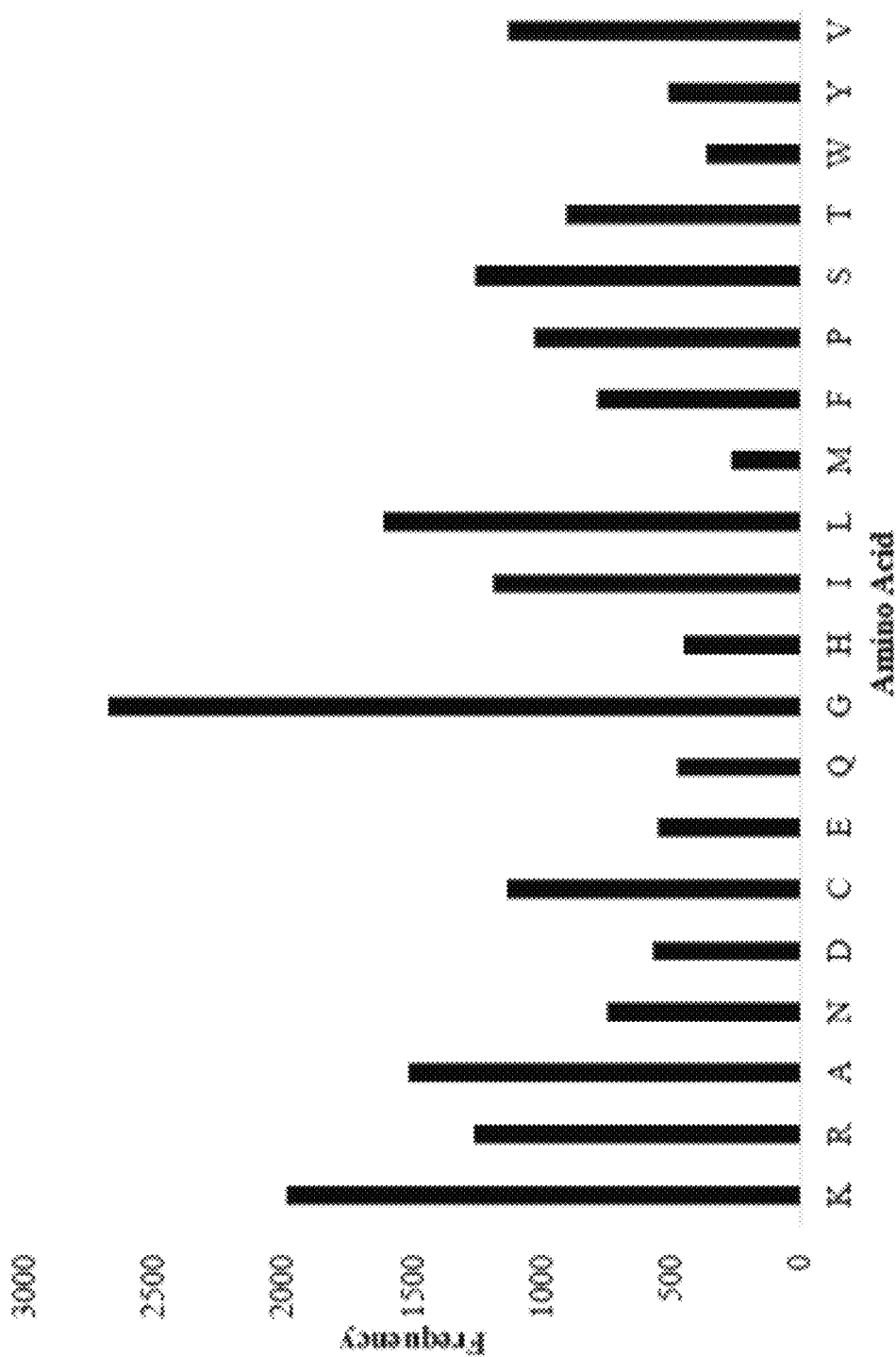

Ab initio filtering technology was used to design PHNX-2 through PHNX-5. The first filter used was length where the length of each peptide was calculated using the Excel formula "LEN" as shown in FIG. 2A. From Dataset 1, the most commonly represented sequence length selected was 13 and 14 which occurred 27 and 25 times, respectively. Large AMPs>20mer were initially not selected due to difficulty in their synthesis as well as the high likelihood of larger peptides forming complex 3-dimensional structures. The next filter we applied was the frequency of each amino acids in the entire dataset. MS Excel was used to conduct this analysis, the formula "LEN" was used where for example, =LEN(G2)-LEN(SUBSTITUTE(G2, "K," " ") enabled Excel to calculate the number of times K occurs in each peptide. This was repeated for each amino acid in Dataset 1. FIGS. 2A-2D illustrate the amino acid frequency in Dataset 1. Based on the ab initio method, the amino acids were grouped as: non-polar hydrophobic, (A, C, I, L, M, F, W, and V), polar uncharged (N, Q, S, T, and Y), small turn residues (G and P), acidic (D, E) and basic (K, R, and H).

Figure 2C:
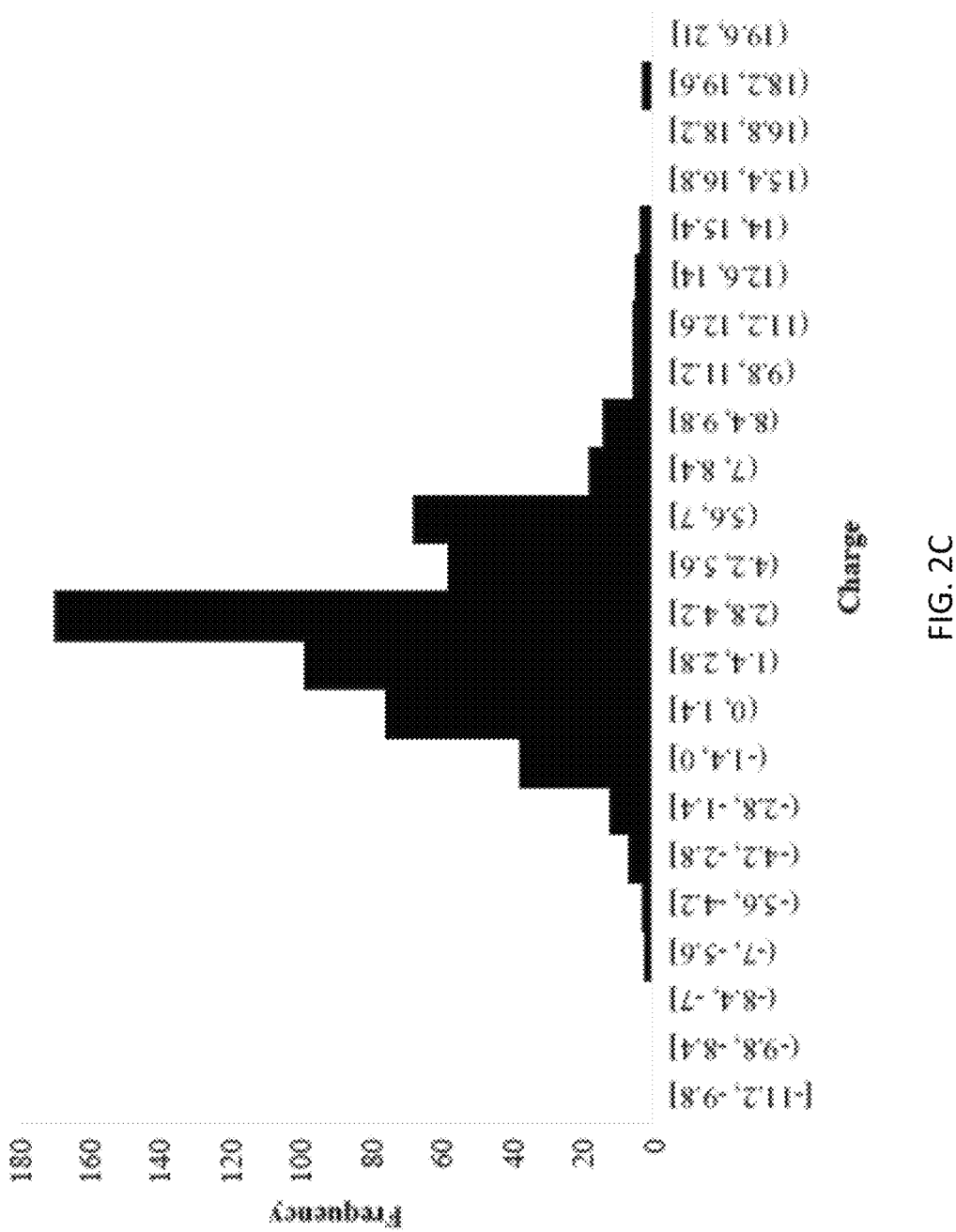
Figure 2D:
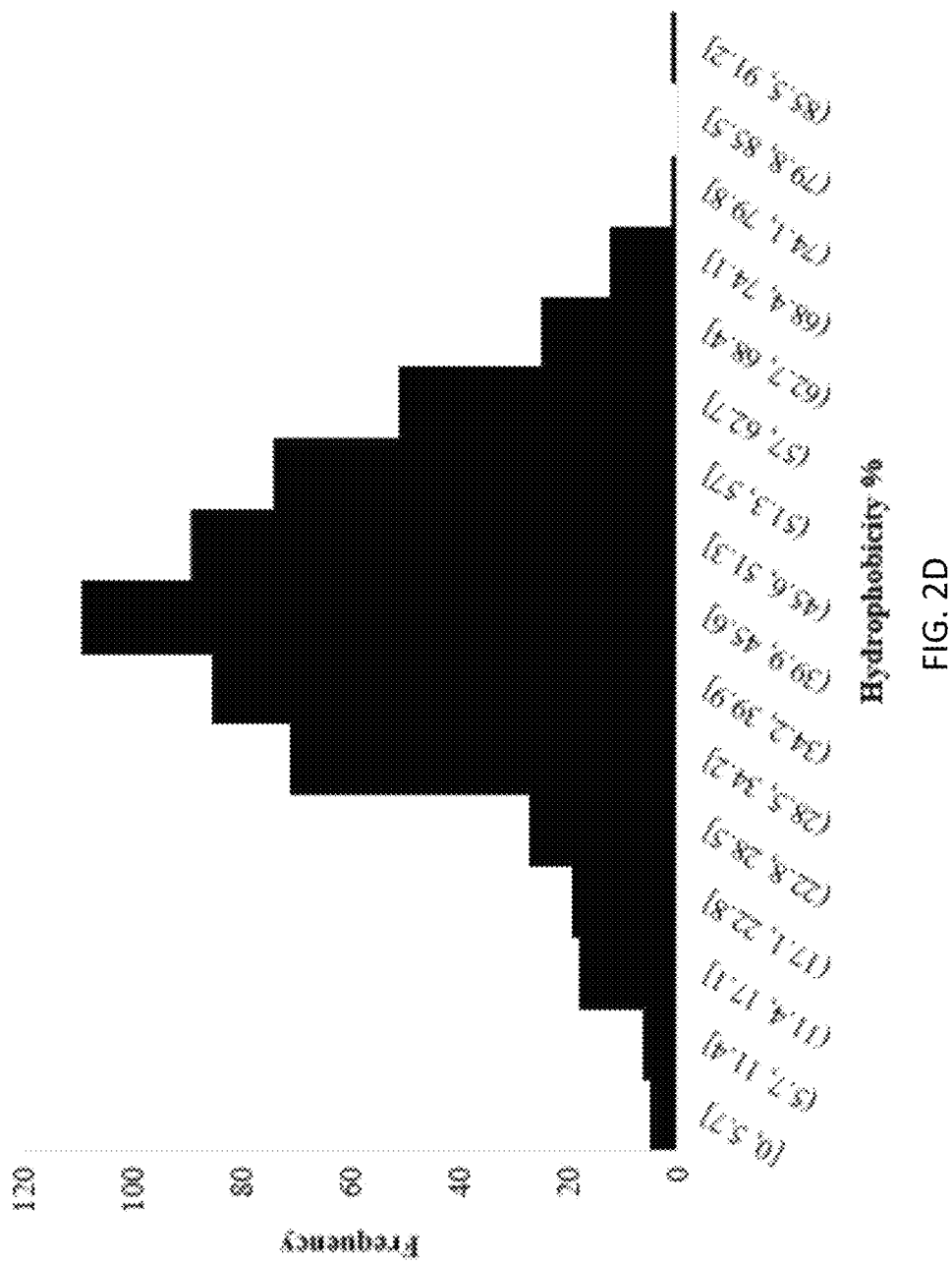
Figure 3B:
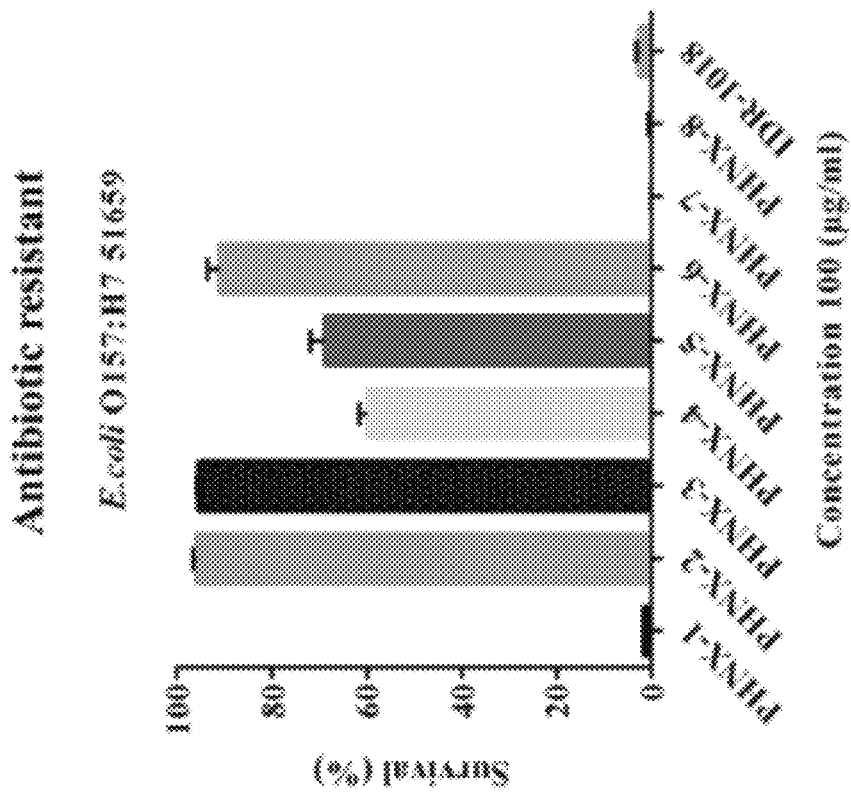
FIGS. 3A-3D show antibacterial screening of PHNX-peptides and controls (IDR-1018 and BF-CATH) at 100 µg/ml.
Figure 3A:
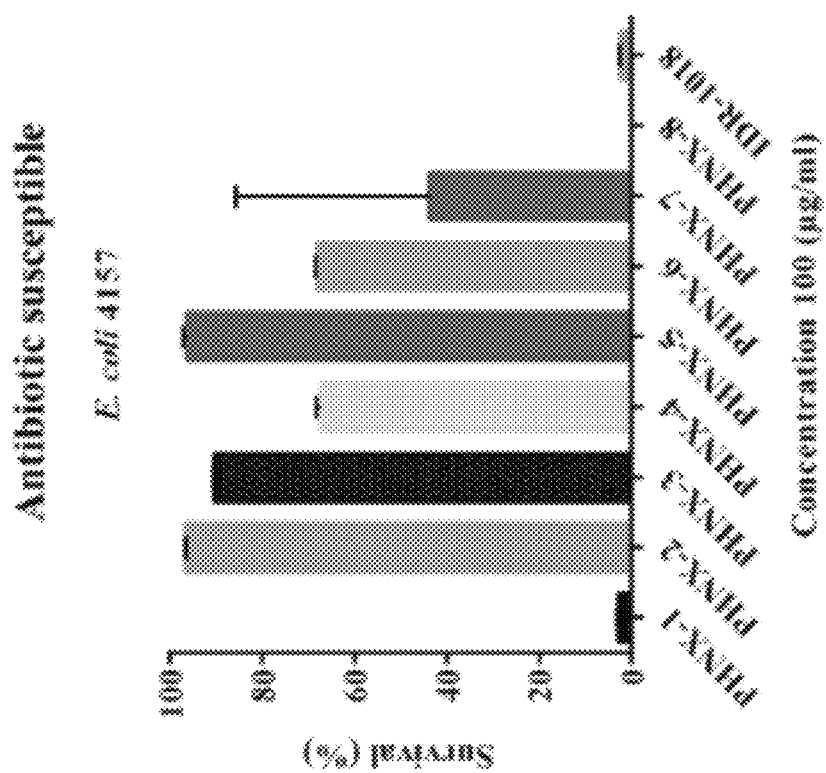
Figure 3D:
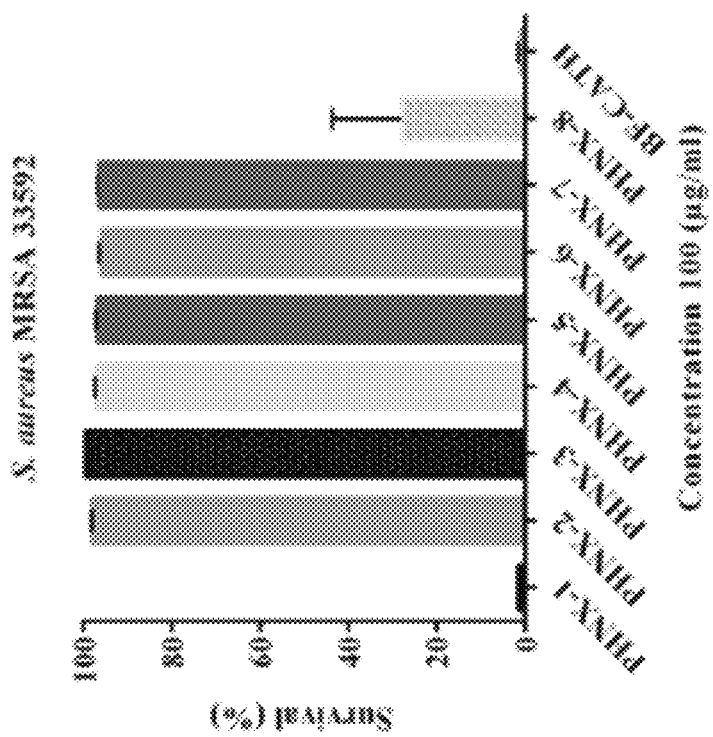
Figure 3C:
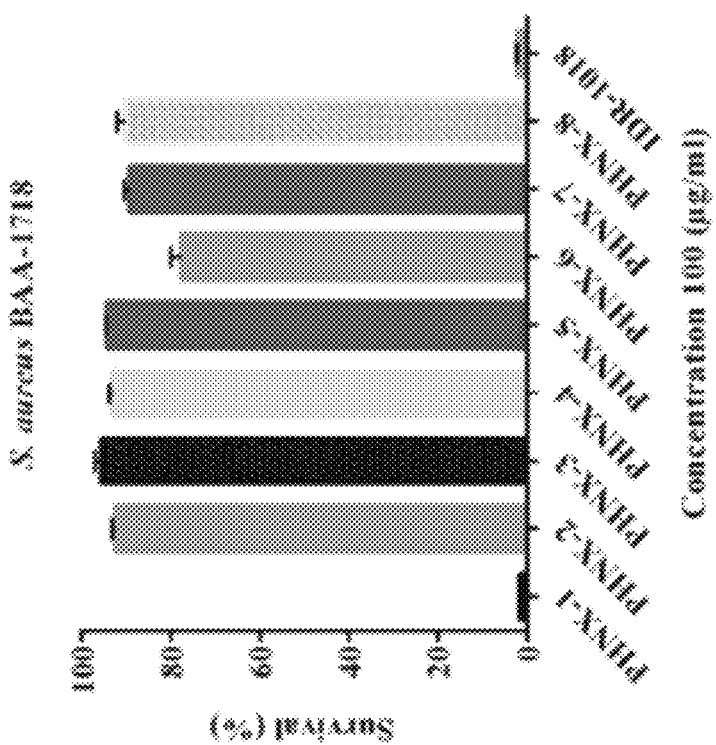
Figure 4B:
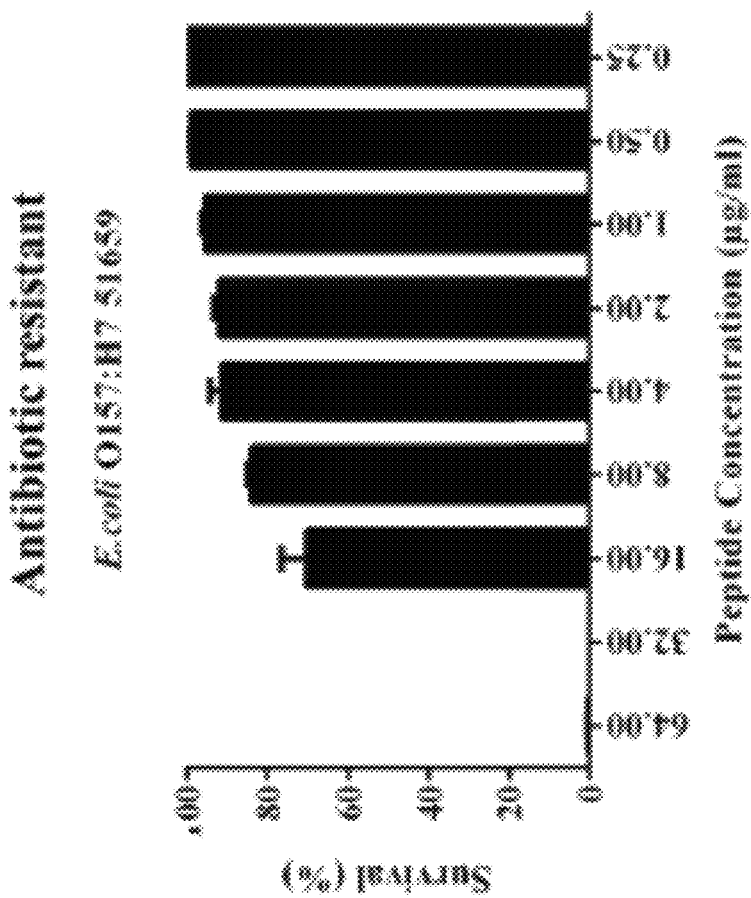
FIGS. 4A-4D show minimum inhibitory concentration (MIC) of PHNX-1 against four strains of bacteria.
Figure 4A:
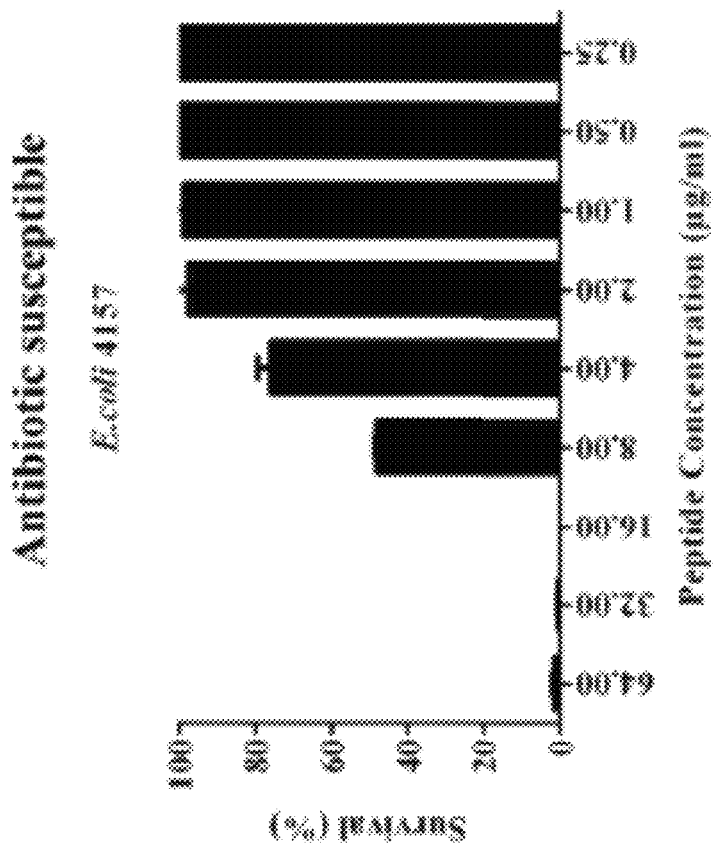
Figure 4D:
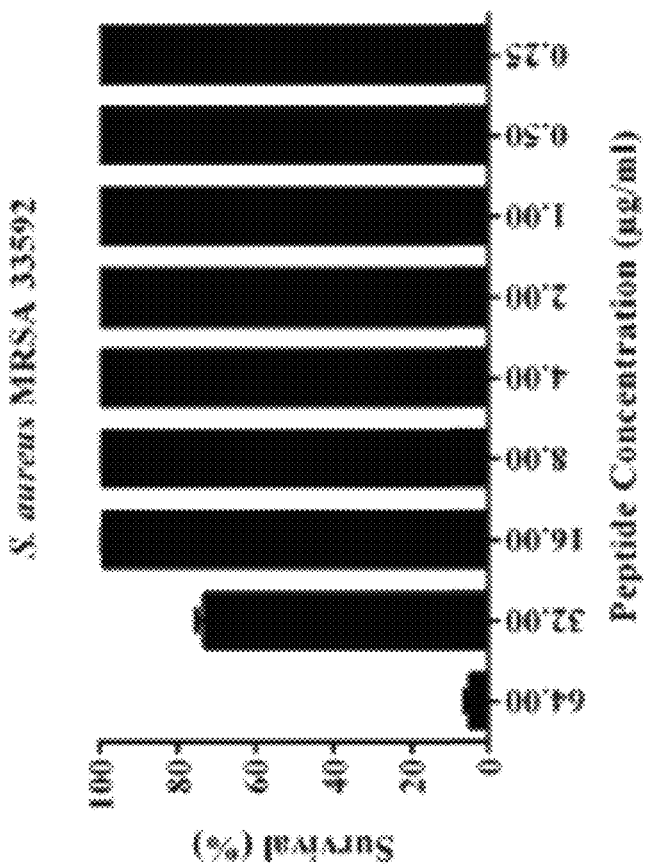
Figure 4C:
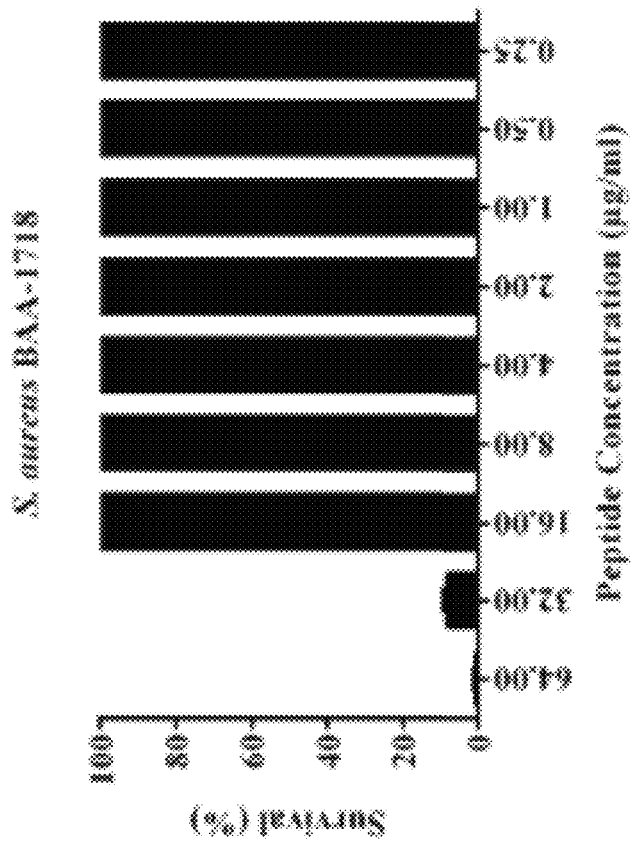
Figure 5A:
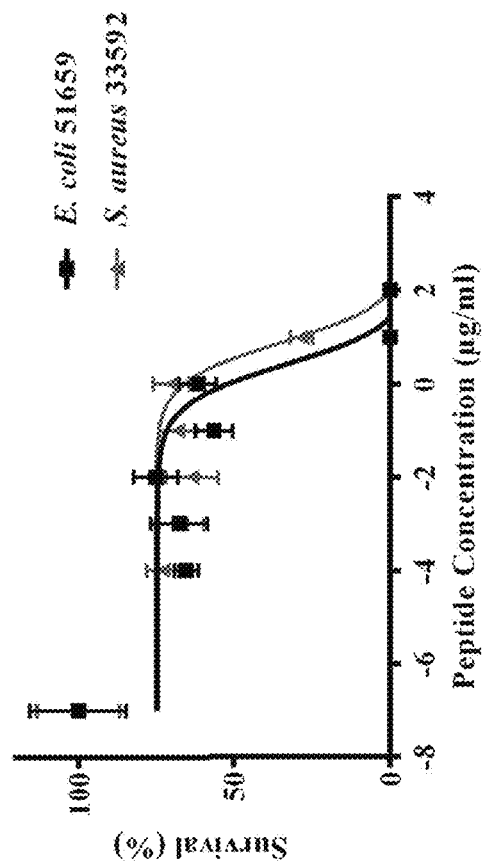
FIGS. 5A-5D show half maximal effective concentration ($EC_{50}$) of antibacterial peptides against antibiotic resistant $E.$ $coli$ O157:H7 51659 and $S.$ $aureus$ MRSA 33592.
Figure 5B:
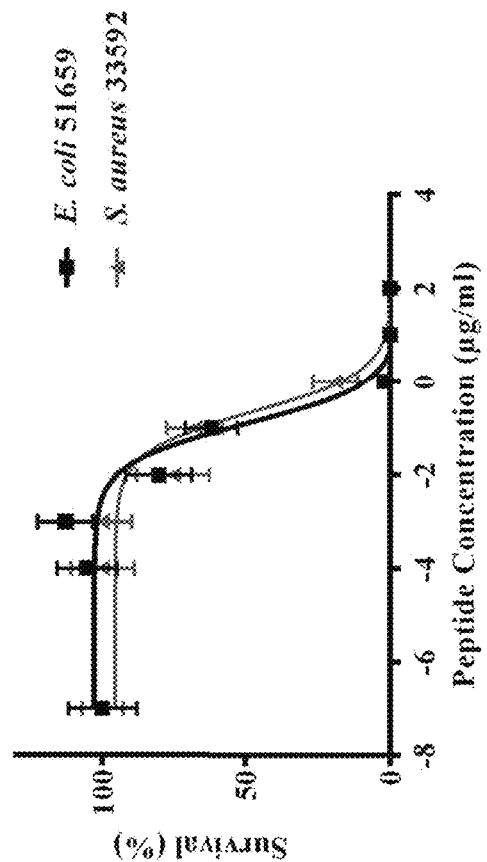
Figure 5C:
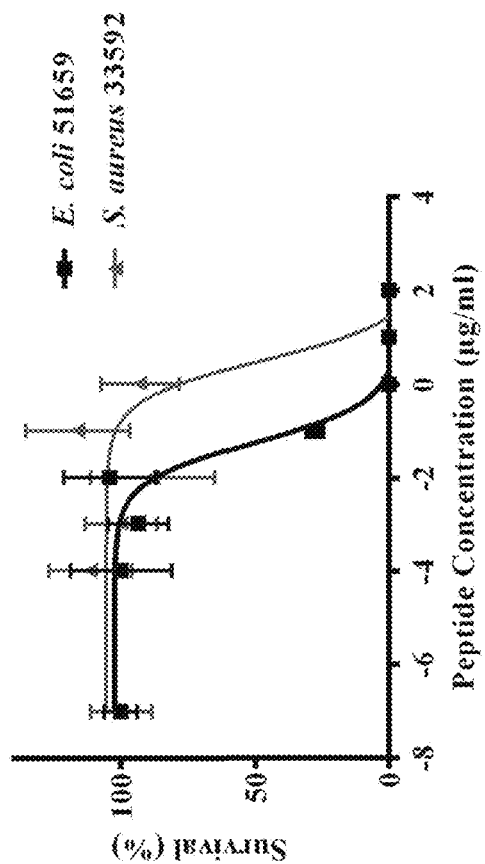
Figure 5D:
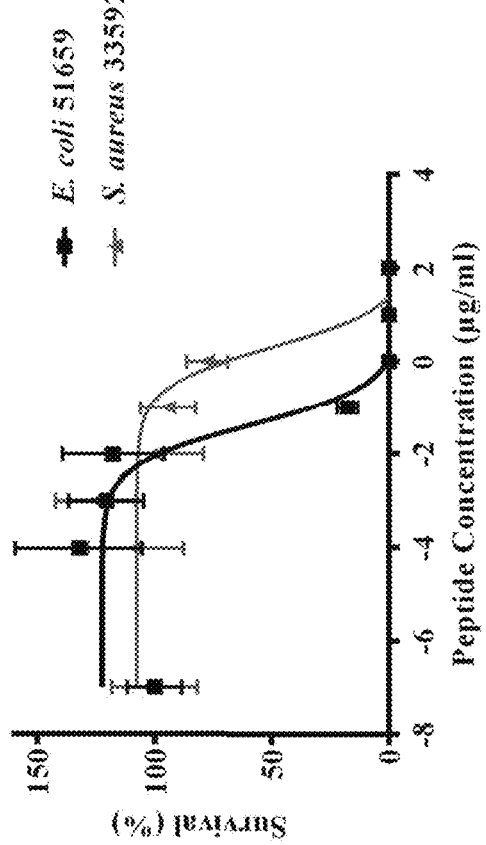

The next filter applied was charge and R-Studio "Peptides" package was used to obtain the charge of the AMPs (Osorio et al., 2015; RStudio Team, 2020). The code used was Charge (sequence, pH=7, pKscale="Lehninger"). The most commonly occurring charge in Dataset 1 was C4 (FIG. 2C). The hydrophobicity of the amino acids was then measured using the ab initio method where the hydrophobicity percentage was calculated by dividing the total number of hydrophobic residues (based on the Kyte and Doolittle scale) by the total amino acids per AMP (Kyte and Doolittle, 1982; Mishra and Wang, 2012). In addition, tryptophan was also included by APD due to its strong interfacial preference. The most commonly occurring hydrophobicity percentages were 43 and 44% (FIG. 2D). Thus, the major criteria for designing novel AMPs were obtained: peptide length of 13 or 14 amino acids with a C4 charge and 43-44% hydrophobicity. Thus, the designed AMP sequence should contain 5 and 6 hydrophobic residues for 13 and 14-residue long AMP, respectively. Furthermore at least 4 K (most frequently occurring positively charged amino acid in the dataset) will be needed to provide a C4 charge which would leave 4 residues in each sequence as the neutral G or S amino acids (both of which were equally represented in the dataset). Hence, a regular expression for a 13 residue AMP with 43-44% hydrophobicity, C4 charge to result in a helical secondary structure would be: FXXKXXKGGKGGK (SEQ ID NO: 11), wherein X in position 2 is isoleucine or leucine, X in position 3 is isoleucine or leucine, X in position 5 is isoleucine or leucine, and X in position 6 is isoleucine or leucine. The BLOSUM substitution matrix was used to substitute residues per position and the amino acid frequency per position was then used to rationally design PHNX-2 through PHNX-5 (Henikoff and Henikoff, 1992). At position 1, the amino acid F was chosen as it was the most frequent residue represented followed by I and R and resulted in designing synthetic AMPs with the highest score of predicted antimicrobial activity. The regular expression above was selected as the synthetic AMPs resulted in an alpha-helix structure to allow it to transverse the bacterial membrane.

PHNX-1

After designing AMPs using the ab initio method, we wanted to use a purely data-based approach to develop a synthetic AMP; hence, we proposed combining DFT method with an additional filter termed positional analysis. This analysis consists of analyzing the residues at each position within a subset of AMPs to identify the most frequently occurring amino acid residue per position. Initially, a 20-residue length cutoff was established to prevent designing an AMP with structural complexities and 12-, 13-, and 14-residue length AMPs were selected from Dataset 1 as they occurred 20, 27, and 25 times, respectively. MS Excel was used to calculate the amino acid occurring most frequently per position to design a 14-residue long AMP called PHNX-1. To determine the amino acid per position, the Excel formula MID [$B2, COLUMNS ($B$2:C$2), position number] was used followed by COUNTIF ($D$2:$D$16, B19) to count the frequency of each residue per position. Finally, the formula MAX was used to calculate the residue that occurred most frequently per position. Table 1 illustrates the most frequently occurring amino acid per position by analyzing each position to design a 14-residue long AMPs in Dataset 1 which enabled the design of PHNX-1.

TABLE 1

Positional analysis results where the amino acid with the highest frequency per position was assessed and resulted in the design of PHNX-1.

| Position | Amino Acid | Frequency |
|---|---|---|
| 1 | Phenylalanine (F) | 18 |
| 2 | Leucine (L) | 15 |
| 3 | Leucine (L) | 19 |
| 4 | Lysine (K) | 18 |
| 5 | Isoleucine (I) | 23 |
| 6 | Valine (V) | 14 |
| 7 | Alanine (A) | 10 |
| 8 | Leucine (L) | 11 |
| 9 | Leucine (L) | 21 |
| 10 | Lysine (K) | 14 |
| 11 | Lysine (K) | 21 |
| 12 | Lysine (K) | 20 |
| 13 | Leucine (L) | 16 |
| 14 | Leucine (L) | 10 |

PHNX-6 Through PHNX-8

Dataset 2 was used to design PHNX-6, PHNX-7 and PHNX-8. Due to the excellent prediction results obtained for PHNX-1, positional analysis was again conducted, however, the 20-mer cut off used in the previous method was eliminated to ensure that an AMP with a potentially greater activity against Gram-negative bacteria was not excluded from this list. The most frequently occurring lengths in the entire dataset [13, 25, and 28 (frequency 13, 13, and 15, respectively)] were chosen from Dataset 2. Positional analysis (FIGS. 7A-7D) was conducted on three separate subsets consisting of 13-, 25-, and 28-residue long AMPs to design PHNX-6, PHNX-7, and PHNX-8.

Determining Similarity and Properties of PHNX Antimicrobial Peptides

The similarity of the synthetic antimicrobial peptides to existing naturally or synthetically designed peptides was assessed using the APD3's Calculation and Prediction tool and the AMPs with the greatest similarity were incorporated into Table 2 (Wang et al., 2016). APD3 tools1 were used to calculate the length charge, Wimley-White whole-residue hydrophobicity of the peptide (the sum of whole-residue free energy of transfer of the peptide from water to POPC interface), Boman index, APD3 defined hydrophobicity ratio and Grand Average Hydropathy Value (GRAVY) of the designed AMPs where the FASTA format of the AMPs was input under "Calculation and Prediction," ran and the properties were incorporated into the table shown in FIG. 8 (Wang et al., 2016). The Hydrophobic moment (μH), Hydrophobicity (H) were obtained from HeliQuest2 where the AMP sequence was incorporated and the parameter window size was set as "Full" to obtain the two properties (Gautier et al., 2008).

TABLE 2

Synthetically designed sequences of the PHNX AMPs and their similarity to peptides within the APD3 database.

| SEQ ID NO: | Name | Sequence | Similarity |
|---|---|---|---|
| 1 | PHNX-1 | FLLKIVALLKKKLL | 60% AP02977 (Temporin-PE) |
| 2 | PHNX-2 | FGKLLKLGKGLGG | 50% AP00739 (Caeridin-a1) |
| 3 | PHNX-3 | FGKLLKLGKGLKG | 50% AP03169 [Peptide LDKA (synthetic)] |
| 4 | PHNX-4 | FLLKLGLGKKKLL | 57.14% AP03112 [DFT503 (synthetic)] |
| 5 | PHNX-5 | FLIKILKGGKGGK | 50% AP02842 (Temporin-MS4) |

TABLE 2-continued

Synthetically designed sequences of the PHNX AMPs and
their similarity to peptides within the APD3 database.

| SEQ ID NO: | Name | Sequence | Similarity |
|---|---|---|---|
| 6 | PHNX-6 | FIGAIASYLKKFR | 69.23% AP00405 (Ranatuerin 6) |
| 7 | PHNX-7 | GVVDIIKGAGKKFAKGLAGKIANKK | 62.96% AP02598 (Ocellatin-PT4) |
| 8 | PHNX-8 | GLMDTVKNAAKNLAGQLLDKIKCKITGC | 96.42% AP01507 (Ranatuerin-2CPc) |

Bioinformatics Prediction of Antibacterial Activity

The following AMP prediction tools used to predict the antibacterial activity: AxPEP3 Deep-AmPEP30 and RFAmPEP30 that uses two algorithms, convolutional neural network and random forest, respectively, to predict<30-residue AMPs; CAMPR34 using the algorithms SVM, RF, Discriminate analysis and ANN; CLASSAMPS algorithms SVM and RF and; DBAASP6 that uses a machine learning algorithm using the Moon and Fleming scale to assess the physiochemical properties of the AMPs (Hydrophobic moment, Charge density and depth-dependent potential) (Joseph et al., 2012; Waghu et al., 2016; Yan et al., 2020; Pirtskhalava et al., 2021). The FASTA formatted sequence of each AMP was input, run and the results were incorporated into the table shown in FIG. 9.

Bacterial Strains

*Staphylococcus aureus* ATCC 33592 (MDR) and BAA-1718, *E. coli* ATCC 51659 (MDR) and 4,157 were purchased from the American Type Culture Collection (Manassas, VA, United States). All strains are reference strains. Bacteria were grown in Tryptic Soy Broth (BD 211825), except *E. coli* 4157 which was grown in Nutrient Broth (Difco 234000), overnight in a shaking incubator (37 C). Bacteria were aliquoted, mixed with glycerol (final concentration of 20% of glycerol) and frozen at −80 C and enumerated via serial dilution and plating prior to experimentation.

Peptide Synthesis

All peptides were synthesized using Fmoc chemistry. Peptides were provided at >95% purity, and the purity and structure were confirmed with RP-HPLC and ESI-MS.

Minimum Inhibitory Concentration Antimicrobial Activity Assay

The antibacterial screening test of the peptides (n=3) was first determined at a final peptide concentration of 100 μg/ml and a final bacterial concentration of 5×10⁵ CFU/mL in Difco Mueller Hinton Broth (BD 275730) in a 96 well plate. The plate was incubated for 16-20 h at 37 C and then read on a spectrophotometer at OD600 nm. Peptides which showed full inhibition of growth at 100 μg/ml were taken forward for full MIC testing. Wells containing medium only were used as sterility control, in the wells around the edge of the plates. LL-37 was used as a control in the first run of experiments against the MDR bacterial strains (Turner et al., 1998). However, it showed >64 μg/ml against *S. aureus*. Hence, we searched for active alternative controls that are experimentally validated against MDR *E. coli* and *S. aureus* and selected IDR-1018 (Wieczorek et al., 2010; Jahnsen et al., 2013) and BF-CATH (Tajbakhsh et al., 2018). The sequence of BF-CATH was derived from DBAASP database listed as cathelicidin-BF-34 with the following sequence:

(SEQ ID NO: 9)
KRFKKFFRKLKKSVKKRAKEFFKKPRVIGVSIPF (Tajbakhsh et al., 2018; Pirtskhalava et al., 2021). This differs slightly from the sequence for BF-CATH in APD3. AP00896:

(SEQ ID NO: 10)
KRFKKFFKKLKKSVKKRAKKFFKKPRVIGVSIPF

The full range MIC activity testing of the peptides was then determined as previously reported using the Mueller Hinton Broth (BD 275730) in a 96 well plate following the CLSI protocol (Wiegand et al., 2008). Enumerated bacteria were diluted in MHB and 50 ul of 1×10⁶ CFU/mL (5×10⁴ CFU) was added to each well with 50 ul of a decreasing series of twofold peptide concentration. The plate was incubated for 16-20 h at 37 C and then read on a spectrophotometer at OD600 nm. Readings of less than 10% of the untreated control were marked as "clear wells" for calling the MIC (Schwarz et al., 2010). Student's t-test was used to determine whether points were statistically different.

EC$_{50}$ Antimicrobial Activity Assay

The antimicrobial activity of the PHNX peptides and LL-37 (AnaSpec 61302) against bacteria was determined as previously described (Barksdale et al., 2016, 2017). Briefly, 1×10⁵ CFU per well of bacteria were incubated with different peptide concentrations (n=3) in a 50-ul solution of 10 mM sodium phosphate buffer (3 h, 37 C). Serial dilutions were then prepared in 1× Dulbecco's PBS and 8 ul of each dilution was spotted in triplicate on Tryptic Soy Agar plates, which were incubated (37 C, 24 h) and CFUs were counted (Barksdale et al., 2016, 2017). Bacterial survival at each peptide concentration was calculated based on the ratio of the number of colonies on each experimental plate and the average number of colonies observed for assay cultures lacking peptide. The peptide concentration required to kill 50% of the viable bacteria in the assay cultures (EC$_{50}$) was determined by plotting percent survival as a function of the log of peptide concentration (log μg/ml) and fitting the data using GraphPad Prism 6 (GraphPad Software Inc., San Diego, CA, United States). For the purpose of graphing, samples that had no peptide (0 μg/ml) are plotted at 1×10⁻⁷ μg/ml peptide. EC$_{50}$ values were determined by fitting the data from the antimicrobial assays to a standard sigmoidal dose-response curve. Errors were reported as a standard error of the mean within 95% confidence interval of the deviation from the mean of the log EC$_{50}$ values. Student's t-test was used to determine whether points were statistically different. Wells containing only 10 mM sodium phosphate buffer were used as sterility control. IDR-1018 was used as a positive control in this experiment as it demonstrated activity under MIC conditions against the antibiotic-resistant strains.

Hemolysis Analysis

To measure the hemolytic activity of peptides, 2% human red blood cells were added to various dilutions of peptide reconstituted in PBS in a sterile U-bottom polystyrene 96 well plate (Dean et al., 2011). The commercially obtained, deidentified human RBCs (BIOIVT Westbury, NY) were prepared as follows: 1 mL of K2EDTA whole blood from a healthy donor was centrifuged at 1,600 g for 10 min and plasma was discarded. The remaining RBCs were washed 4 times with 1 ml 1×PBS (HyClone), then the pallet after the last wash was resuspended with 750 ul of 1×PBS. 2% RBCs suspension was prepared by adding 200 ul of washed cells to 9.8 mL of 1×PBS. 50 ml of 2% RBCs were added to each well (n=3) containing diluted peptides resulting in final peptide concentration of 100, 10, and 1 µg/ml. 2% RBCs with 1×PBS alone served as the negative control (No peptide), and 2% RBC in deionized water as the positive control, leading to full lysis. The plate was incubated for 1 h at 37 C and then centrifuged at 1,000 rpm for 2 min. The supernatant was transferred to a fresh regular 96 well plate and read at OD540 as previously reported (Dean et al., 2011). Student's t-test was used to determine whether points were statistically significant.

Example 1: Similarity to Existing Antimicrobial Peptides

Positional analysis comprises analyzing residues at each position within a dataset of AMPs to identify the most frequently occurring amino acid residue per position.

Due to the lack of new antimicrobials being developed to combat Gram-negative infections, we used computational approaches combined with traditional laboratory benchtop assays to develop and assess novel AMPs against drug resistant and antibiotic susceptible strains of Gram-negative bacteria. The ab initio database filtering technology (DFT) method (Mishra and Wang, 2012) combined with positional analysis was used on two datasets obtained from APD3, which resulted in the design of 8 novel, synthetic AMPs termed PHNX, referring to the Phoenix, a powerful bird arising from the ashes. The databases and methods used to design the peptides are described in the "Materials and Methods" section. Table 2 illustrates the sequences of the synthetically designed PHNX AMPs as well as their similarity to existing naturally occurring or synthetically designed AMPs in the APD3 database (Wang et al., 2016).

The similarity of PHNX AMPs to existing AMPs with proven antibacterial activity ranged between 50 and 96% for PHNX-1 through PHNX-8. The peptides PHNX-1, -2, and -5 through -8 were the most similar to naturally occurring AMPs, suggesting that they may be active against Gram-negative bacteria. PHNX-1 shares 60% similarity with Temporin-PE, a naturally occurring AMP found in the skin secretions of the common water frog (Pelophylax kl. *Esculentus*) with antimicrobial activity against *S. aureus* (MIC 2 uM), MRSA (MIC 4 uM) *E. coli* (MIC 16 uM), *Enterococcus faecalis* (*E. faecalis*) (MIC 8 uM), and *Candida albicans* (*C. albicans*) (MIC 4 uM)(Sang et al., 2018). Similarly, PHNX-2 and PHNX-5 shared 50% similarity with Caeridinal (an AMP found in the skin secretions of the Australian White's Tree Frog, *Litoria caerulea* with a diverse antimicrobial activity against *S. aureus* NCTC10788 (MIC 8 uM), MRSA NCTC12493 (MIC 16 uM), *E. faecalis* NCTC12697 (MIC 32 uM), *E. coli* NCTC10418 (MIC 32 uM), and *C. albicans* NCYC1467 (MIC 32 uM) and Temporin-MS4, an AMP found in a frog (*Hylarana maosuoensis*), with activity against Gram-positive bacteria *S. aureus* ATCC 25923 (MIC 9.4 uM), *E. faecalis* 981 (MIC 18.8 uM), and *Nocardia asteroides* 201118 (MIC 4.7 uM) (Wang X. et al., 2017; Li et al., 2018). PHNX-8 (designed using positional analysis on Dataset 2) had a high degree of similarity (96.42%) to a naturally occurring AMP Ranateurin 2CPc (Wang et al., 2016) found in the skin secretion of New World frog (*Lithobates capito*) (Conlon et al., 2009).

PHNX-6 and PHNX-7 were 69.23 and 62.96% similar to Ranateurin-6 and Ocellatin-PT4, respectively (Wang et al., 2016). Ranateurin-6 and Ocellatin-PT4 are AMPs found in the skin secretions of the American bull frog (*Rana catesbeiana*) and the ceara white-lipped frog (*Leptodactylus pustulatus*) with weak activity against Gram-positive *S. aureus* (MIC 100 uM) and Gram-negative *E. coli* ATCC 25922 (MIC 80 uM), with no hemolysis observed for either AMP (Goraya et al., 1998; Marani et al., 2015). PHNX-3 and PHNX-4 demonstrated similarity to a set of synthetically designed AMPs Peptide LDKA and DFT503. These AMPs were developed using Simulation-Guided Rational de Novo Design (Peptide LDKA) as well as ab initio design (DFT503)(Chen et al., 2019; Mishra et al., 2019). Peptide LDKA has demonstrated activity against *E. coli* (MIC 35 uM) and *S. aureus* (10 uM) and interestingly also shares similarity to another ab initio designed AMP called DFTamP1 (Wang et al., 2016; Chen et al., 2019). DFT503 has demonstrated antibacterial activity against *S. aureus* USA300 LAC (MIC 3.1 uM), *S. aureus* M838-17, *Enterococcus faecium* V286-17 (anti-VRE, MIC 3.1-6.2 uM) with no activity against Gram-negative bacteria and also shares 71% similarity with DFTamP1 (Mishra et al., 2019).

All synthetically designed PHNX peptides expressed a minimum of 50% similarity to existing AMPs with proven antimicrobial activity further strengthening our argument that that there is a strong likelihood that PHNX AMPs will demonstrate activity in vitro but are still unique and novel peptides.

Example 2: PHNX Antimicrobial Peptides Properties

After assessing the similarity and differences of PHNX AMPs, the properties of the AMPs were calculated, and the table in FIG. 8 summarizes the properties of the PHNX AMPs. Computational analyses have demonstrated that net charge and amphipathicity are the most important physiochemical properties that statistically differentiate anti-Gram-negative AMPs from others (Wang C. K. et al., 2017). AMPs designed using ab initio database filtering technology method (PHNX-2 to -5) were each 13 residues long and AMPs designed using positional analysis (PHNX-1, PHNX-6, PHNX-7, and PHNX-8) were 14, 13, 25, and 28 residues long, respectively. All PHNX AMPs were positively charged (to allow them to associate with the negatively charged bacterial membrane) with the majority of the peptides having a charge of +3 (C3) and +4 (C4) and an outlier of +6 (C6) observed in PHNX-7. Studies have demonstrated that high cationicity in synthetically designed AMPs correlate with increased in vitro antibacterial activity and minimal cytotoxicity up to a threshold of +8 (C8) beyond which an increase in hemolytic activity is observed (Bahar and Ren, 2013; Lee et al., 2019). However, lower cationicity has been associated with in vivo active peptides (Mishra et al., 2019). Thus, the PHNX AMPs with the cationic charges between C3 through C6 will hopefully exhibit antimicrobial effects with minimal hemolytic activity.

The ideal AMP needs to be amphipathic to allow transport in an aqueous environment and interaction with bacterial lipid bilayer membrane. Hence, we used six separate measures to assess the PHNX AMPs hydrophobicity and amphipathicity including: the Wimley—White hydrophobicity, Hydrophobic moment <μH>, Hydrophobicity, Grand average of hydropathy index score, the Boman index to assess protein binding potential and finally, the APD3 defined hydrophobic ratio. The Wimley-White whole-residue hydrophobicity was positive for PHNX-5, PHNX-7, and PHNX-8 and negative for others indicating that PHNX AMPs ranged between neutral to slightly hydrophilic (Wimley and White, 1996). Additionally, PHNX AMPs (except PHNX-7) had positive GRAVY scores indicating hydrophobicity; however, the scores were relatively close to neutral suggesting some amphipathicity. PHNX-1 had the highest GRAVY score of 1.46.

The Boman index, which assesses protein binding potential, was negative for PHNX-1 to -5 indicating hydrophobicity but positive for PHNX-6 to -8. It should be noted, however, that all Boman index scores (positive or negative) were near 0 for all AMPs except PHNX-1 (−1.5 kcal/mol). This was expected as AMPs typically do not bind other proteins but instead transverse and disrupt the bilayer membrane leading to membrane rupture. The APD-defined "hydrophobic ratio" was 38% for rationally PHNX-2, -3, and -5 which were all ab initio designed AMPs. PHNX-4, also an ab initio designed AMP, had a higher hydrophobic ratio of 53%. PHNX-1 had the highest hydrophobic ratio of 71% and the ratio for the longer AMPs, PHNX-7 and -8, was 44 and 46%, respectively. PHNX-6, designed using positional analysis, had a hydrophobic ratio of 46%. The APD-defined hydrophobic ratio ordered the peptides similarly to the calculation of H, the "Hydrophobicity" calculation for the peptides whose values range from −1.01 to 2.25 (Gautier et al., 2008). PHNX-1 and -4 had the highest scores (0.81 and 0.62, respectively) and however, all the AMPs had scores <1 indicating amphipathicity. The hydrophobic moment, μH, a value between 0 and 3.26 which indicates the amphipathicity of the AMPs perpendicular to its axis (Gautier et al., 2008) was higher than 0.5 for PHNX-2, -3, and -6. The other PHNX AMPs had a lower hydrophobic moment where PHNX-1 was 0.41 μH and PHNX-4, -7, and -8 had a hydrophobic moment below 0.4 μH.

Overall, we observed a diversity in APD3-defined hydrophobic ratios with PHNX-4 and PHNX-1 as the two outliers, with high ratios compared to the other AMPs designed rationally or using positional analysis. Based on the other five statistics to measure the hydrophobicity, PHNX AMPs overall are likely amphipathic structures with low protein binding potential (evidenced by the Boman index), neutral to slightly hydrophilic AMPs (Wimley—White whole-residue hydrophobicity), hydrophobic but close to neutral GRAVY and a Hydrophobicity (H) score ranging close to neutral indicating amphipathicity. The amphipathicity of the peptides can also be observed in the measurements of the hydrophobic moment (μH, FIG. 8) and in the helical wheel projections shown in FIGS. 11A-11C.

Example 3: PHNX Antimicrobial Peptides Antimicrobial Activity Prediction

A variety of prediction tools including different machine learning algorithms [support vector machine (SVM), random forest (RF), artificial neural network (ANN) and discriminate analysis (DA)] were used to assess PHNX AMPs predicted antimicrobial activity. Using a diverse set of tools ensured that the PHNX AMPs function was assessed against a variety of AMP datasets to increase the power of the prediction. The antimicrobial activity was predicted using four prediction tools across nine algorithms with the resulting scores listed in FIG. 9. PHNX-1 scored high (probability≥0.92) for antimicrobial activity across all prediction tools and algorithms. PHNX-2, -3, and -6 were predicted as AMPs but had at least one score below 0.85 (PHNX-2 scored 0.73 and 0.54 using Deep-AmPEP and CAMPR3-RF; PHNX-3 scored 0.77 and 0.73 using Deep-AmPEP and CAMPR3-RF and PHNX-6 scored 0.70 using RF-AmPEP). The other PHNX AMPs were predicted as non-AMPs or not antimicrobial by at least one out of the nine predicting algorithms. PHNX-4 and -5 were predicted as non-AMP by DBAASP which uses a machine learning algorithm based on physio-chemical properties of AMPs but scored >0.85 as predicted by the other algorithms (Pirtskhalava et al., 2021). PHNX-7 and -8 were classified as not antimicrobial by CLASSAMP, however, PHNX-8 was predicted to be an AMP with a probability >0.85 using other algorithms and PHNX-7 scored≥0.84 by all algorithms.

Overall, 100% of PHNX AMPs were predicted to be AMPs by at least seven of the nine algorithms, 75% predicted as AMPs by eight algorithms and 12.5% predicted by all 9 algorithms. Thus, we can conclude it is likely that all PHNX AMPs, especially PHNX-1, are antimicrobial, with antibacterial activity, based on the scores established by multiple algorithms that use different training datasets to make their predictions.

Example 4: PHNX In Vitro Inhibition of Representative Gram-Positive and Gram-Negative Bacteria We then tested the in vitro inhibition of MDR and antibioticsusceptible E. coli and S. aureus strains against the PHNX AMPs. These two bacteria are frequently utilized as model organisms to test the activity of AMPs and were selected to demonstrate whether the designed peptides met the design criteria of anti-Gram-negative activity, as well as the broader "antibacterial" activity.

Screening

The peptides were first screened at a high concentration of 100 μg/ml against MDR and antibiotic susceptible strains, and the active peptide against these bacteria qualified for minimal inhibitory concentration (MIC) determination (FIGS. 3A-3D). IDR-1018 and BF-CATH were used as controls in screening against MDR E. coli and S. aureus where the two control AMPs demonstrated 100% bactericidal activity at 100 μg/ml concentration. We then assessed the MIC of the following PHNX AMPs, PHNX-1 which inhibited the growth of all bacterial strains, PHNX-8 which showed activity against the E. coli strains. PHNX-7 slightly inhibited MDR E. coli 51659, however, all other AMPs demonstrated no antibacterial activity against the MDR or antibiotic susceptible strains in the screen.

Minimum Inhibitory Concentration

PHNX-1, with the predicted score of ≥0.92 probability of having antimicrobial activity, had a MIC of 32 and 64 μg/ml against MDR E. coli 51659 and S. aureus 33592, respectively, as shown in FIGS. 4A-4D. Antibiotic susceptible strains were sensitive to PHNX-1 with a MIC of 16 μg/ml against E. coli 4157 and 32 μg/ml against S. aureus BAA-1718. PHNX-7 exhibited a high MIC value of >64 μg/ml against MDR E. coli 51659. PHNX-8 had a MIC of 64 μg/ml against MDR *E. coli* 51659 and a MIC of 32 µg/ml against antibiotic susceptible strain of *E. coli* 4157 without any activity against the antibiotic resistant or susceptible strains of Gram-positive bacterium *S. aureus*. FIG. 10 presents the MIC values of all the PHNX peptides against drug resistant and antibiotic susceptible strains of *E. coli* and *S. aureus* where LL-37, BF-CATH and IDR-1018 were used as the control AMPs against the four bacterial strains, as they have known activity against these bacteria. Although we used different strains, BFCATH showed a strong antimicrobial activity against *E. coli*, similar to the levels previously reported of 2.3 µg/ml against *E. coli* ATCC 25922 and it was not very effective against *S. aureus* (Wang et al., 2008). Similarly, IDR-1018 showed good activity against the strains tested here (approximately 16 µg/ml), similar to previously reported activities (Wieczorek et al., 2010; Jahnsen et al., 2013).

Additionally, while LL-37 was initially selected for use as a control against antibiotic-resistant strains of *E. coli* and *S. aureus*, our data demonstrated poor antimicrobial activity of >64 µg/ml against MRSA, similar to previously reported activities (Turner et al., 1998). We added a column to the table of FIG. 10 summarizing the AMP predictions from FIG. 9 to enable comparisons between the predictions and the in vitro experimental data.

$EC_{50}$ Results

We next tested the PHNX AMPs against drug-resistant strains of *E. coli* and *S. aureus* under low-salt conditions to eliminate the probability of salt-mediated inactivation which would prevent the AMP from inhibiting bacterial growth. Interestingly, all PHNX AMPs, except PHNX-2 and -3, demonstrated activity inhibiting the growth of MDR *E. coli* and MRSA under low-salt conditions. These assays determine the half-maximal effective concentration ($EC_{50}$) for antibacterial activity under 10 mM sodium phosphate conditions, following published protocols (Barksdale et al., 2016). PHNX-1 demonstrated the highest activity, as expected based on the MIC and bioinformatic prediction results, with an $EC_{50}$ of 0.12 and 9.22 µg/ml against MDR *E. coli* and MRSA, respectively (FIGS. 5A-5D). PHNX-7, a highly cationic AMP, and PHNX-8, the longest AMP with a C-terminal rana box, demonstrated an $EC_{50}$ of 0.04 and 0.06 µg/ml against MDR *E. coli* and 2.09 and 3.31 µg/ml against MRSA, respectively. PHNX-6, also designed using positional analysis, demonstrated an $EC_{50}$ of 2.60 and 7.95 µg/ml against MDR *E. coli* and MRSA. Finally, PHNX-4 and PHNX-5 demonstrated an $EC_{50}$ of 2.91 and 4.95 µg/ml against MDR *E. coli* and 4.85 and >10 µg/ml against MRSA. It should also be noted that PHNX-7 and -8, designed using positional analysis on Dataset 2, demonstrated a lower $EC_{50}$ against Gram-negative MDR *E. coli* compared to the Gram-positive *S. aureus*, as shown in FIGS. 5A-5D, further confirming our hypothesis that using a "Gram-negative only" dataset resulted in rationally designing AMPs with higher activity against Gram-negative bacteria. FIG. 11 outlines the $EC_{50}$ results of the MDR *E. coli* and *S. aureus* strains against all the 8 PHNX peptides including the 95% confidence intervals, and the $EC_{50}$ results also presented in micromolar (uM) units. PHNX-4, -5, -6, and -8 had a larger range within the 95% confidence interval of $EC_{50}$ against MRSA (for PHNX-4, -6, and -8) and *E. coli* (for PHNX-5) indicating greater variability in the concentration of the peptide required to inhibit bacterial growth and thus, increased likelihood of variable activity for the above peptides.

Figure 6:
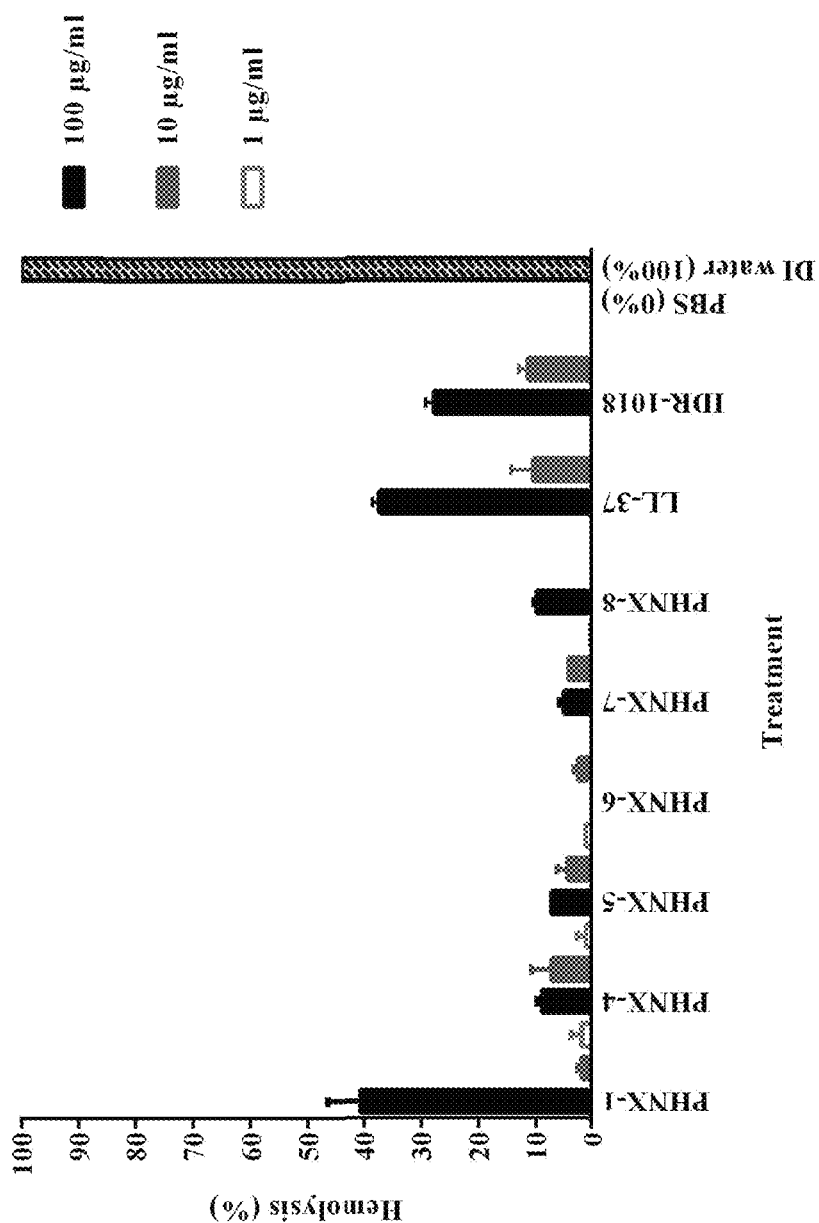
FIG. 6 shows hemolysis of the PHNX peptides against human red blood cells collected in EDTA with LL-37, deionized (DI) water and IDR-1018 were used as the controls. All PHX AMPs demonstrated hemolytic activity not significantly different from or lower than the controls.
Figure 7A:
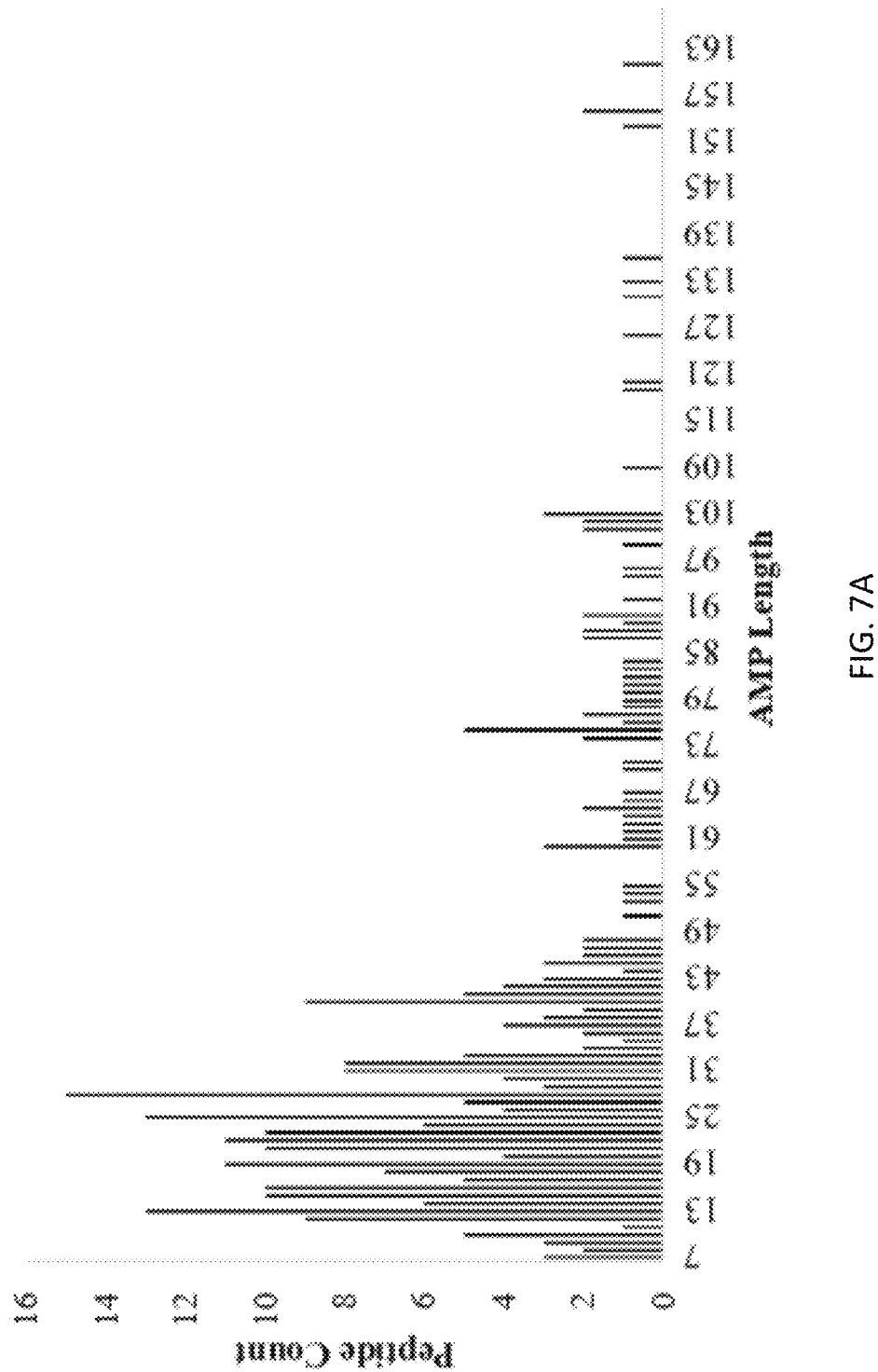
FIGS. 7A-7D show statistics of AMP properties obtained from APD3.
Figure 7B:
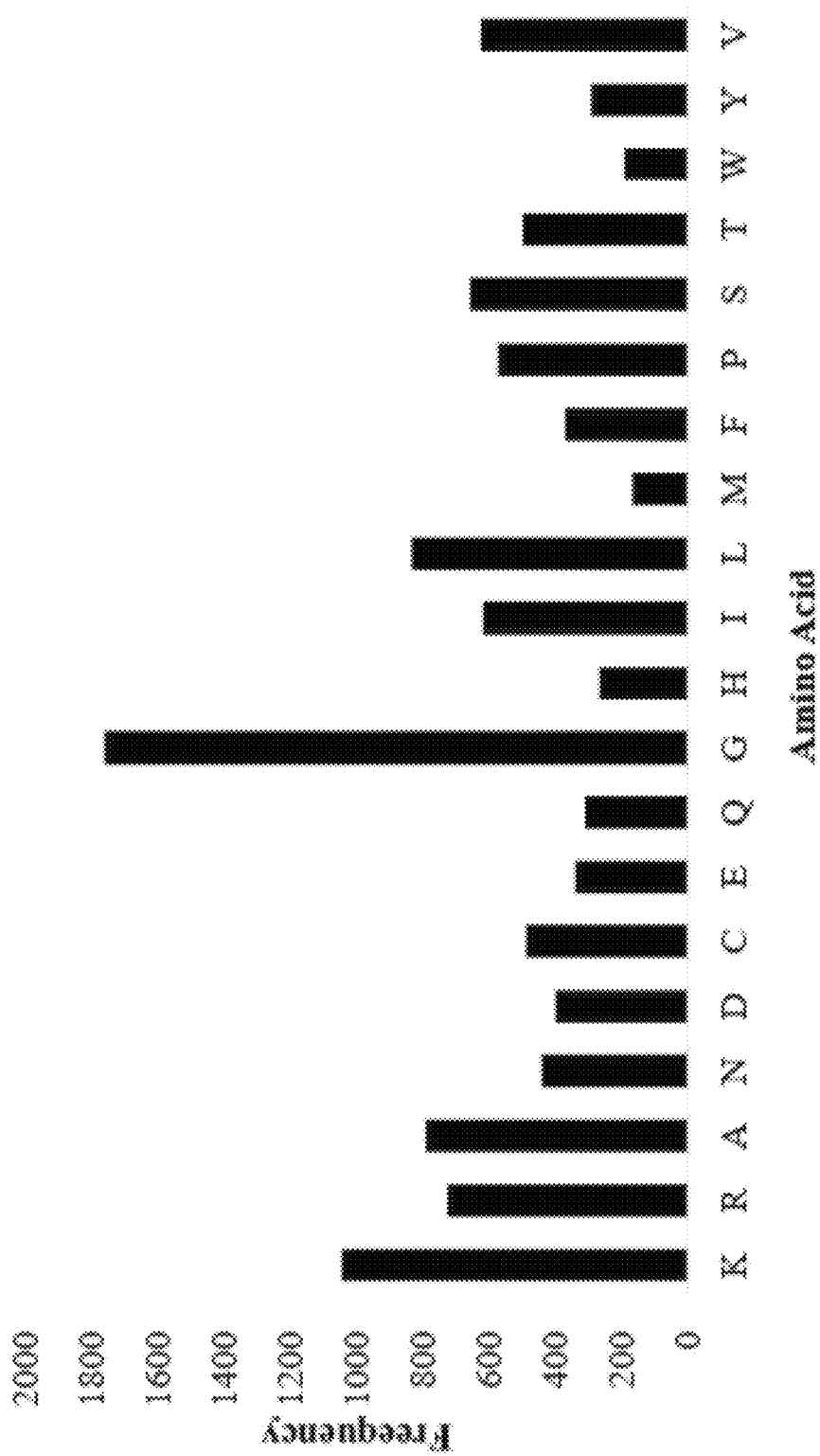
Figure 7C:
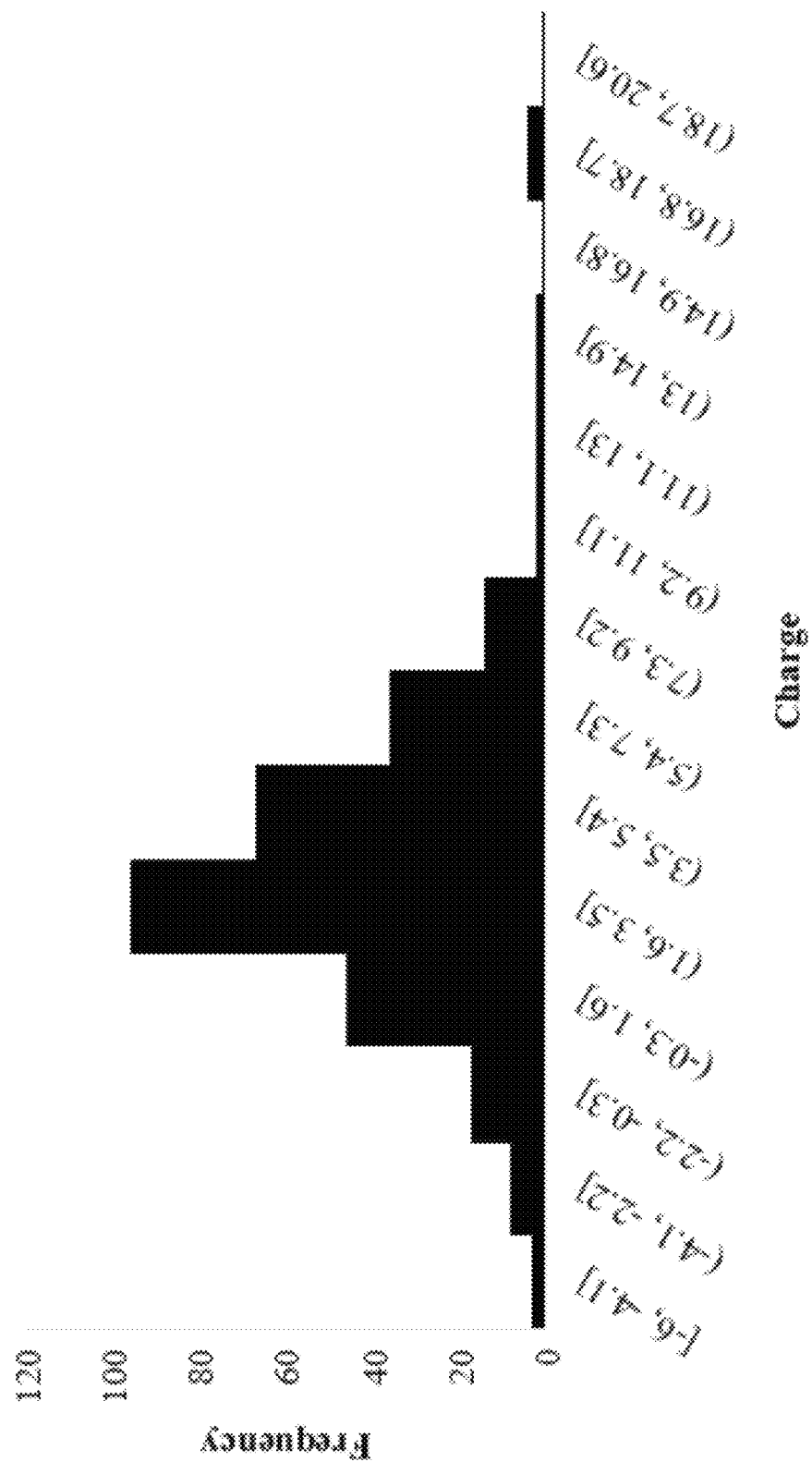
Figure 7D:
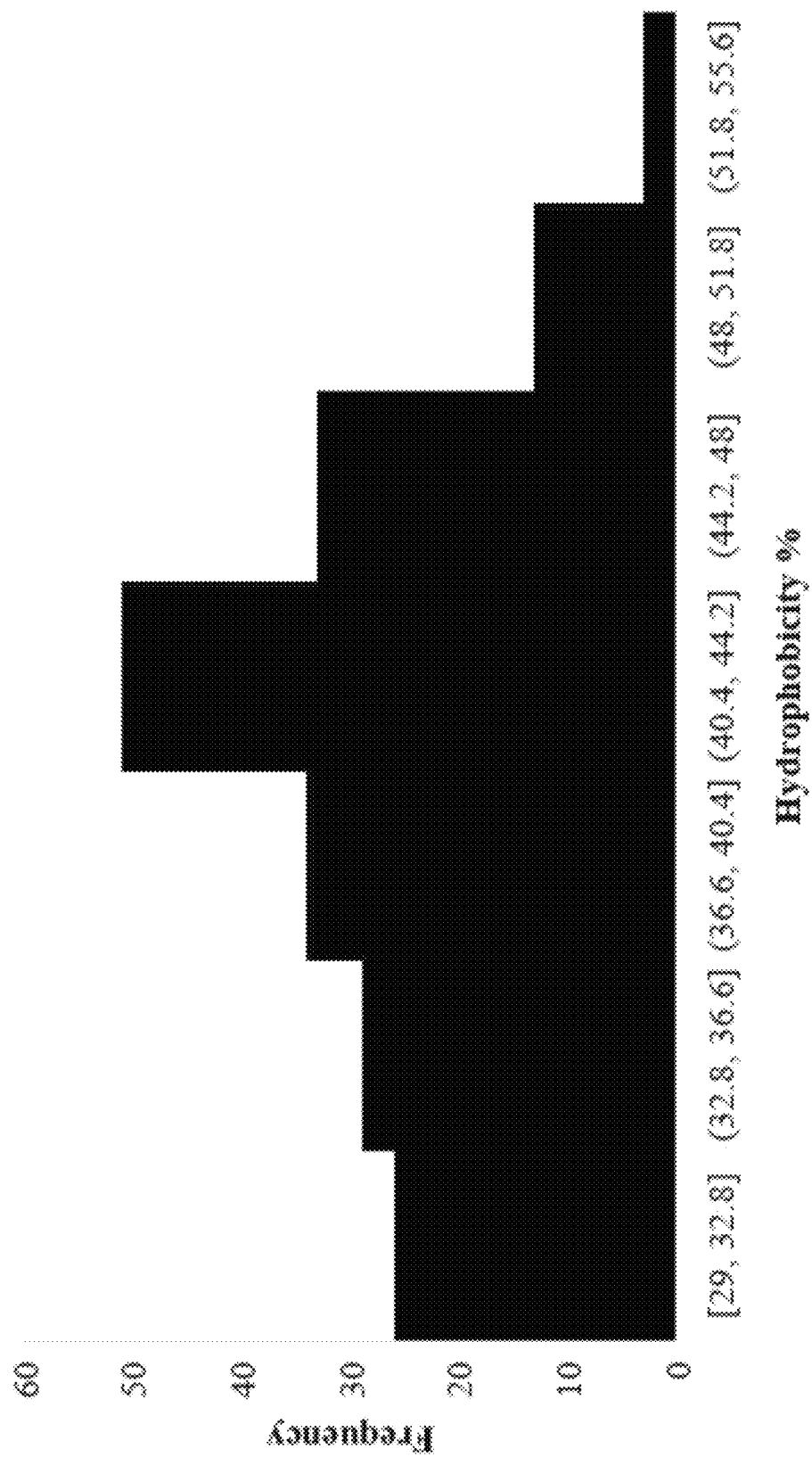
Figure 12A:
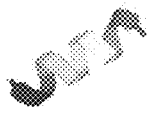
Figure 12C:
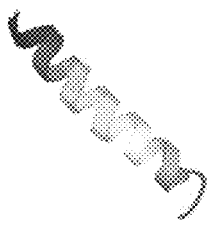

Example 5: Hemolytic Activity and Therapeutic Potential of the PHNX Antimicrobial Peptides After establishing MIC and $EC_{50}$ activity, we tested the hemolytic potential of the synthetically designed PHNX AMPs. PHNX-1 demonstrated the highest hemolytic activity (approximative 40% hemolysis) at 100 µg/ml with minimal hemolysis at 10 and 1 µg/ml. PHNX-4, -5, -7, and -8 demonstrated higher hemolytic activity at 100 µg/ml sequentially decreasing at 10 and 1 LL-37 and IDR-1018 were the two controls used against human red blood cells (RBCs) to test hemolysis and demonstrated a similar pattern sequentially reducing hemolytic activity with approximately 40% hemolysis at 100 µg/ml, 10% at 10 µg/ml and negligible hemolysis at 1 µg/ml. This level of hemolysis is significantly higher than is seen with defribrinated sheep and horse blood, which may reflect the fragility of the RBCs collected in EDTA as an anticoagulant. Since the PHNX peptides showed antimicrobial activity between 16 and 64 µg/ml, this range is covered by the hemolysis testing. All PHNX AMPs outperformed the control peptides with overall lower hemolytic activity at each of the three concentrations. FIG. 6 demonstrates the hemolytic activity of PHNX AMPs. As the hemolytic concentrations are not significantly different than the MIC concentrations (within an order of magnitude), these PHNX peptides probably need additional development in future work to increase their therapeutic index. Additionally, future work on using the MIC concentration of each AMP with a narrower range of AMP concentrations to assess cytotoxicity would result promising results. The therapeutic index may also serve as an in vitro filter to identify the peptides with the best cell selectivity. A high therapeutic index indicates high safety and minimal toxicity in vivo (Jiang et al., 2014; Mahlapuu et al., 2016; Wang C. K. et al., 2017).

DISCUSSION

In this new method, ab initio database filtering technology (DFT) was combined with a new step of positional analysis to computationally design novel synthetic antimicrobial peptides (AMPs) termed PHNX AMPs. The APD3 dataset of AMPs was parsed to generate a set of peptides with a narrow spectrum of activity against Gram-negative bacteria. This dataset was used in our computational approach to design new peptides with the hypothesis that the resulting peptides would have activity against Gram-negative bacteria. Our results show that 3/8 peptides (PHNX-1, -7, and -8) have antimicrobial activity against Gramnegative bacteria at 100 µg/ml or less and 6/8 (PHNX-1, -4, -5, -6, -7, and -8) have activity against Gram-negative bacteria under low-salt conditions ($EC_{50}$) at 10 µg/ml or less. Without wishing to be bound by theory, it appears that designing peptides by this method to be active against Gram-negative bacteria leads to a high number of peptides with that desired activity.

Overall, the PHNX AMPs demonstrated >50% similarity to existing AMPs (naturally occurring or synthetically designed) with computed properties traditionally observed in AMPs with antibacterial activity. PHNX-7 and PHNX-8 were the two outliers, PHNX-7 had high cationicity which predicted higher antibacterial activity with low hemolytic potential and PHNX-8, an AMP uniquely characterized by a "Rana box" which consists of a cyclic disulfide bridge at the C-terminus due to flanking cysteine residues separated by other four or five residues (Bao et al., 2018). AMPs with the Rana box domain share a structural analogy with Polymyxin, a cyclic peptide antibiotic used to treat multi-drug resistant infections caused by *Pseudomonas* spp. and *Acinetobacter* spp. where studies have demonstrated the importance of the structure within the Rana box which may correlate with an AMPs antimicrobial activity (Kozi'c et al., 2015). This correlated with our results where PHNX-7 and -8 had the lowest $EC_{50}$ and the highest activity against Gram-negative organisms compared to all other AMPs.

We studied whether measures of hydrophobicity and amphipathicity are important for activity. PHNX-1 (0.41 μH) had a hydrophobic moment closer to the Apo AMPs we previously discovered, which have also demonstrated antibacterial activity (Barksdale et al., 2016). In the data we obtained however, no obvious correlation was observed between the hydrophobicity and amphipathicity scores and the PHNX AMP's in vitro activity. The "APD3 defined hydrophobic ratio (%)" somewhat correlated with $EC_{50}$ activity, as most of the peptides with $EC_{50}$ activity had greater than 40% APD3 defined hydrophobic ratio (%). It is generally thought that amphipathic AMPs typically demonstrate antibacterial activity, especially if helical. Some AMPs, like LL-37, can be membrane-active where the AMPs are disordered until interacting with the bacterial membrane to form an amphipathic helix penetrating the bacterial membranes (Hollmann et al., 2018).

Bioinformatics based AMP prediction can be complex as each prediction tool uses a different algorithm with a different training dataset which can result in a diversity of predicted AMP probabilities. Hence, we used nine different predictors and although all PHNX AMPs were predicted as antimicrobial, in vitro testing demonstrated that only PHNX-1 and PHNX-8 had antibacterial activity under high-salt conditions against the MDR strain of *E. coli*. However, it should be noted that PHNX-1 demonstrated the highest probability of having antimicrobial activity across all predictors with the highest overall consensus for predicted activity. This reflected our laboratory results where PHNX-1 demonstrated antibacterial activity under both MIC and $EC_{50}$ conditions against Gram-positive and Gram-negative bacteria. Under low-salt conditions, all AMPs, except PHNX-2 and -3, demonstrated activity against the drug resistant strains of *E. coli* and *S. aureus* and no PHNX AMP was hemolytic at 10 μg/ml. PHNX-2 and -3 had the lowest probability of antimicrobial activity as predicted by DeepAmPEP and CAMPR3-RF algorithms compared to the other PHNXAMPs, and the lab results demonstrated no activity against any bacterial strains. Prior studies have established CAMPR3-RF as the analytical tool with the best performance due to a large training dataset resulting in high accuracy in its predictions and our study further corroborated that result (Gabere and Noble, 2017). The $EC_{50}$ results also imply that salt-mediated inactivation may have played a role in preventing the PHNX AMPs from inhibiting bacterial growth under high salt conditions. Studies have demonstrated that serum and salt mediated inactivation has prevented antibacterial activity of peptides in vivo with short amphipathic helical AMPs having the highest likelihood of salt-resistance (Mohanram and Bhattacharjya, 2016). PHNX-1, a short helical AMP, demonstrated activity under high salt conditions and thus presents as a candidate with expected in vivo activity and the potential for further development as a potential clinical therapeutic.

Overall, the PHNX AMPs designed using the novel positional analysis method (PHNX-1, -6, -7, and -8) demonstrated higher antibacterial activity against Gram-negative bacteria than the AMPs designed using only the ab initio DFT method (PHNX-2 to -5). In our study, using the DFT approach, the BLOSUM substitution matrix was used to substitute amino acids with equal frequency within the dataset; however, these substitutions may not have resulted in equivalent activity. Additionally, our approach in designing these AMPs combined a rational design element with positional analysis; for example, the decision to choose F at position 1. Additional residue substitution at this position may improve in vitro activity. PHNX-1 and PHNX-6 through -8 were designed using positional analysis method (frequency per position), which is a data-only approach and resulted in demonstrated in vitro activity against the MDR bacterial strains. Our hypothesis that using a dataset of AMPs with activity against Gram-negative bacteria would enable the ab initio design of synthetic peptides with higher activity against Gram-negative bacteria was proven. All PHNX AMPs demonstrated slightly higher activity against MDR and antibiotic susceptible strains of Gram-negative *E. coli* compared to the Gram-positive *S. aureus*. Although PHNX AMPs were active against Gram-positive *S. aureus*, every AMP had better activity against *E. coli*, supporting our design approach of designing a Gram-negative active peptide. PHNX-1 had a lower MIC against *E. coli* when compared to *S. aureus* and PHNX-8 had no activity against *S. aureus* but demonstrated reasonable MIC results against the Gram-negative *E. coli*. The MIC results were further supported under low-salt $EC_{50}$ conditions where PHNX-1 and PHNX-4 though -8 demonstrated uniformly lower $EC_{50}$ results against the Gram-negative MDR strain when compared to the Gram-positive MDR strain.

We have thus established a method to computationally design AMPs against a narrow spectrum class of bacteria (Gram-negative). This study confirms that the database filtering technology is likely to generate peptides with desired activity by starting from a defined set of candidates annotated in the APD3 database. Different from the original study where the most probable parameters were used to design a potent peptide against mainly Gram-positive methicillin-resistant *S. aureus* (MRSA), our designed peptides are primarily active against Gram-negative bacteria based on the inclusion criteria in the original datasets. Of note is that the peptides designed against Gram-positive bacteria have less cationic amino acids than the peptides we designed here. In the original DFT approach, the anti-Gram-positive peptides were generally of +1 (C1) charge, while, for our approach, the peptides most commonly had a charge of +4 (C4).

Our approach of conducting data analysis on a pre-selected sub-set of AMPs with activity against Gram-negative bacteria to determine trends and frequency of amino acids resulted in novel AMPs with lab-tested in vitro activity against drug-resistant strains of bacteria. This combination of in silico design and in laboratory testing to validate the in silico predictions has proven highly successful. This approach can be used to design a variety of antimicrobial peptides against different strains or classes of bacteria, viruses and fungi to result in novel AMPs with a narrow spectrum of activity. Using a larger library of peptides may aid in designing variations of AMPs with predicted narrow and/or broad-spectrum of activity to further validate our design approach. Although our peptides demonstrated activity against MDR *E. coli*, they still need to be further tested against other strains of Gram-negative bacteria to determine the full range of their activity. PHNX AMPs effect on bacterial biofilms also needs to be assessed. Biofilms are a key virulence factor contributing to nosocomial infections and peptide therapeutics with activity against biofilm would be a breakthrough in modern medicine. The PHNX peptides also need some improvements in their hemolytic activity in future studies, perhaps through further rational design to improve their therapeutic index. PHNX AMPs present novel synthetic peptide therapeutics which are a step forward in developing new therapeutics to combat antibiotic resistance.

BIBLIOGRAPHY

Bahar, Ali Adem, and Dacheng Ren. 2013. "Antimicrobial Peptides." *Pharmaceuticals* 6 (12): 1543-75.

Bao, Kaifan, Weiyuan Yuan, Chengbang Ma, Xi Yu, Lei Wang, Min Hong, Xinping Xi, Mei Zhou, and Tianbao Chen. 2018. "Modification Targeting the 'Rana Box' Motif of a Novel Nigrocin Peptide From Hylarana Latouchii Enhances and Broadens Its Potency Against Multiple Bacteria." *Frontiers in Microbiology*.

Barksdale, Stephanie M, Evelyn J Hrifko, Ezra Myung-Chul Chung, and Monique. L van Hoek. 2016. "Peptides from American Alligator Plasma Are Antimicrobial against Multi-Drug Resistant Bacterial Pathogens Including *Acinetobacter Baumannii.*" *BMC Microbiology* 16 (1): 189.

Barksdale, Stephanie M, Evelyn J Hrifko, and Monique L van Hoek. 2017. "Cathelicidin Antimicrobial Peptide from *Alligator Mississippiensis* Has Antibacterial Activity against Multi-Drug Resistant *Acinetobacter Baumanii* and *Klebsiella Pneumoniae.*" *Developmental & Comparative Immunology* 70: 135-44.

Browne, Katrina, Sudip Chakraborty, Renxun Chen, Mark Dp Willcox, David StClair Black, William R Walsh, and Naresh Kumar. 2020. "A New Era of Antibiotics: The Clinical Potential of Antimicrobial Peptides." *International Journal of Molecular Sciences* 21 (19): 7047.

Cardoso, Marlon H, Raquel Q Orozco, Samilla B Rezende, Gisele Rodrigues, Karen G N Oshiro, Elizabete S Candido, and Octavio L Franco. 2020. "Computer-Aided Design of Antimicrobial Peptides: Are We Generating Effective Drug Candidates?" *Frontiers in Microbiology* 10 (January): 3097.

Cepas, Virginio, Yuly Lopez, Estela Muñoz, Dora Rolo, Carmen Ardanuy, Sara Marti, Mariona Xercavins, Juan Pablo Horcajada, Jordi Bosch, and Sara M Soto. 2018. "Relationship Between Biofilm Formation and Antimicrobial Resistance in Gram-Negative Bacteria." *Microbial Drug Resistance* 25 (1): 72-79.

Chen, Charles H, Charles G Starr, Evan Troendle, Gregory Wiedman, William C Wimley, Jakob P Ulmschneider, and Martin B Ulmschneider. 2019. "Simulation-Guided Rational de Novo Design of a Small Pore-Forming Antimicrobial Peptide." *Journal of the American Chemical Society* 141 (12): 4839-48.

Chien-Kuo, Wang, Shih Ling-Yi, and Kuan Y Chang. 2017. "Large-Scale Analysis of Antimicrobial Activities in Relation to Amphipathicity and Charge Reveals Novel Characterization of Antimicrobial Peptides." *Molecules* 22 (11): 2037.

Clinical and Laboratory Standards and Institute (CLSI). n.d. *Methods for Dilution Antimicrobial Susceptibility Tests for Bacteria That Grow Aerobically; Approved Standards-Tenth Edition*. Wayne, Pennsylvania Conlon, J Michael, Mohammed A Meetani, Laurent Coquet, Thierry Jouenne, Jerome Leprince, Hubert Vaudry, Jolanta Kolodziejek, Norbert Nowotny, and Jay. D King. 2009. "Antimicrobial Peptides from the Skin Secretions of the New World Frogs Lithobates Capito and Lithobates Warszewitschii (Ranidae)." *Peptides* 30 (10): 1775-81.

Dean, Scott N, Barney M Bishop, and Monique L van Hoek. 2011. "Natural and Synthetic Cathelicidin Peptides with Anti-Microbial and Anti-Biofilm Activity against *Staphylococcus Aureus.*" *BMC Microbiology* 11 (1): 114.

Gabere, Musa Nur, and William Stafford Noble. 2017. "Empirical Comparison of Web-Based Antimicrobial Peptide Prediction Tools." *Bioinformatics* (Oxford, England) 33 (13): 1921-29.

Gautier, Romain, Dominique Douguet, Bruno Antonny, and Guillaume Drin. 2008. "HELIQUEST: A Web Server to Screen Sequences with Specific α-Helical Properties." *Bioinformatics* 24 (18): 2101-2.

Goraya, Jadvinder, Floyd C Knoop, and J. Michael Conlon. 1998. "Ranatuerins: Antimicrobial Peptides Isolated from the Skin of the American Bullfrog, *Rana Catesbeiana.*" *Biochemical and Biophysical Research Communications* 250 (3): 589-92.

Henikoff, S, and J G Henikoff. 1992. "Amino Acid Substitution Matrices from Protein Blocks." *Proceedings of the National Academy of Sciences of the United States of America* 89 (22): 10915-19.

Hollmann, Axel, Melina Martinez, Patricia Maturana, Liliana C Semorile, and Paulo C Maffia. 2018. "Antimicrobial Peptides: Interaction With Model and Biological Membranes and Synergism With Chemical Antibiotics." *Frontiers in Chemistry* 6 (June): 204.

Jahnsen, Rasmus D., Evan F. Haney, Henrik Franzyk, and Robert E. W. Hancock. 2013. "Characterization of a Proteolytically Stable Multifunctional Host Defense Peptidomimetic." *Chemistry & Biology* 20 (10): 1286-95.

Jiang, Ziqing, Adriana I Vasil, Michael L Vasil, and Robert S Hodges. 2014. "'Specificity Determinants' Improve Therapeutic Indices of Two Antimicrobial Peptides Piscidin 1 and Dermaseptin S4 Against the Gram-Negative Pathogens *Acinetobacter Baumannii* and *Pseudomonas Aeruginosa.*" *Pharmaceuticals* (Basel, Switzerland) 7 (4): 366-91.

Joseph, S, S Karnik, P Nilawe, V K Jayaraman, and S Idicula-Thomas. 2012. "ClassAMP: A Prediction Tool for Classification of Antimicrobial Peptides." *IEEE/ACM Transactions on Computational Biology and Bioinformatics* 9 (5): 1535-38.

Kozić, Mara, Damir Vukičević, Juraj Simunić, Tomislav Rončević, Nikolinka Antcheva, Alessandro Tossi, and Davor Juretić. 2015. "Predicting the Minimal Inhibitory Concentration for Antimicrobial Peptides with Rana-Box Domain." *Journal of Chemical Information and Modeling* 55 (10): 2275-87.

Kyte, Jack, and Russell F Doolittle. 1982. "A Simple Method for Displaying the Hydropathic Character of a Protein." *Journal of Molecular Biology* 157 (1): 105-32.

Lamiable, Alexis, Pierre Thévenet, Julien Rey, Marek Vavrusa, Philippe Derreumaux, and Pierre Tufféry. 2016. "PEP-FOLD3: Faster de Novo Structure Prediction for Linear Peptides in Solution and in Complex." *Nucleic Acids Research* 44 (W1): W449-54.

Lazzaro, Brian P, Michael Zasloff, and Jens Rolff. 2020. "Antimicrobial Peptides: Application Informed by Evolution." *Science* 368 (6490): eaau5480.

Lee, Ping-Chien, Chia-Chun Chu, Yi-Je Tsai, Ya-Chu Chuang, and Feng-Di Lung. 2019. "Design, Synthesis, and Antimicrobial Activities of Novel Functional Peptides against Gram-Positive and Gram-Negative Bacteria." *Chemical Biology & Drug Design* 94 (2): 1537-44.

Li, Lei, Qing Wu, Xi Wang, Huimin Lu, Xinping Xi, Mei Zhou, Chris J Watson, Tianbao Chen, and Lei Wang. 2018. "Discovery of Novel Caeridins from the Skin Secretion of the Australian White's Tree Frog, Litoria Caerulea." *International Journal of Genomics* 2018 (July): 8158453.

Liu, Yuan, Ruichao Li, Xia Xiao, and Zhiqiang Wang. 2019. "Antibiotic Adjuvants: An Alternative Approach to Overcome Multi-Drug Resistant Gram-Negative Bacteria." *Critical Reviews in Microbiology* 45 (3): 301-14.

Mahlapuu, Margit, Joakim Håkansson, Lovisa Ringstad, and Camilla Bjorn. 2016. "Antimicrobial Peptides: An Emerging Category of Therapeutic Agents." *Frontiers in Cellular and Infection Microbiology* 6 (December): 194.

Marani, Mariela Mirta, Flávio Santos Dourado, Patrick Veras Quelemes, Alyne Rodrigues de Araujo, Márcia Luana Gomes Perfeito, Eder Alves Barbosa, Leiz Maria Costa Véras, et al. 2015. "Characterization and Biological Activities of Ocellatin Peptides from the Skin Secretion of the Frog *Leptodactylus Pustulatus*." *Journal of Natural Products* 78 (7): 1495-1504.

Microsoft Corporation. 2018. "Microsoft Excel."

Mishra, Biswajit, Jayaram Lakshmaiah Narayana, Tamara Lushnikova, Xiuqing Wang, and Guangshun Wang. 2019. "Low Cationicity Is Important for Systemic in Vivo Efficacy of Database-Derived Peptides against Drug-Resistant Gram-Positive Pathogens." *Proceedings of the National Academy of Sciences of the United States of America* 116 (27): 13517-22.

Mishra, Biswajit, and Guangshun Wang. 2012. "Ab Initio Design of Potent Anti-MRSA Peptides Based on Database Filtering Technology." *Journal of the American Chemical Society* 134 (30): 12426-29.

Mohanram, Harini, and Surajit Bhattacharjya. 2016. "Salt-Resistant Short Antimicrobial Peptides." *Peptide Science* 106 (3): 345-56.

Okella, Hedmon, John J Georrge, Sylvester Ochwo, Christian Ndekezi, Kevin Tindo Koffi, Jacqueline Aber, Clement Olusoji Ajayi, et al. 2020. "New Putative Antimicrobial Candidates: In Silico Design of Fish-Derived Antibacterial Peptide-Motifs." *Frontiers in Bioengineering and Biotechnology* 8 (December): 604041.

Osorio D, Rondon-Villarreal P, Torres R. 2015. "Peptides: A Package for Data Mining of Antimicrobial Peptides." The R Journal.

Otsuka, Yasunari. 2020. "Drug Discovery: Recent Progress and the Future Potent Antibiotics Active against Multidrug-Resistant Gram-Negative Bacteria" 68 (3): 182-90.

Pirtskhalava, Malak, Anthony A Amstrong, Maia Grigolava, Mindia Chubinidze, Evgenia Alimbarashvili, Boris Vishnepolsky, Andrei Gabrielian, Alex Rosenthal, Darrell E Hurt, and Michael Tartakovsky. 2021. "DBAASP v3: Database of Antimicrobial/Cytotoxic Activity and Structure of Peptides as a Resource for Development of New Therapeutics." *Nucleic Acids Research* 49 (D1): D288-97.

RStudio Team. 2020. "RStudio: Integrated Development for R." Boston, MA

Sang, Mengru, Qinan Wu, Xinping Xi, Chengbang Ma, Lei Wang, Mei Zhou, James F Burrows, and Tianbao Chen. 2018. "Identification and Target-Modifications of Temporin-PE: A Novel Antimicrobial Peptide in the Defensive Skin Secretions of the Edible Frog, Pelophylax Kl. *Esculentus*." *Biochemical and Biophysical Research Communications* 495 (4): 2539-46.

Schwartz, S., et al. (2010). Editorial: assessing the antimicrobial susceptibility of bacteria obtained from animals. J. Antimicrob. Chemother. 65, 601-604.

Silhavy, Thomas J, Daniel Kahne, and Suzanne Walker. 2010. "The Bacterial Cell Envelope." *Cold Spring Harbor Perspectives in Biology* 2 (5): a000414-a000414.

Singh, Harinder, Sandeep Singh, and Gajendra Pal Singh Raghava. 2019. "Peptide Secondary Structure Prediction Using Evolutionary Information." *BioRxiv*, January, 558791.

Tajbakhsh, M. et al. (2018) The antimicrobial potential of a new derivatice of cathelicidin from *Bungarus fasciatus* against methicillin-resistant *Staphylococcus aureus*. J. Microbiol. 56, 128-137.

Tornesello, Anna Lucia, Antonella Borrelli, Luigi Buonaguro, Franco Maria Buonaguro, and Maria Lina Tornesello. 2020. "Antimicrobial Peptides as Anticancer Agents: Functional Properties and Biological Activities." *Molecules* (Basel, Switzerland) 25 (12): 2850.

Torrent, M, D Andreu, M V Nogués, and E Boix. 2011. "Towards the Rational Design of Antimicrobial Peptides: Recent Developments in Computational Tools." In *Science and Technology Against Microbial Pathogens*, 386-89. WORLD SCIENTIFIC.

Turner, J. et al. (1998) Activities of LL-37, a cathelin-associated antimicrobial peptide of human neutrophils. Antimicrob. Agents Chemother. 42, 2206-2214.

Waghu, Faiza Hanif, Ram Shankar Barai, Pratima Gurung, and Susan Idicula-Thomas. 2016. "CAMPR3: A Database on Sequences, Structures and Signatures of Antimicrobial Peptides." *Nucleic Acids Research* 44 (D1): D1094-97.

Wang, Chien Kuo, Ling Yi Shih, and Kuan Y. Chang. 2017. "Large-Scale Analysis of Antimicrobial Activities in Relation to Amphipathicity and Charge Reveals Novel Characterization of Antimicrobial Peptides." *Molecules* 22 (11).

Wang, Guangshun, Xia Li, and Zhe Wang. 2016. "APD3: The Antimicrobial Peptide Database as a Tool for Research and Education." *Nucleic Acids Research* 44 (D1): D1087-93.

Wang, Xiao, Shuguang Ren, Chao Guo, Weiqi Zhang, Xiaoli Zhang, Baowen Zhang, Sihan Li, Jian Ren, Yuhong Hu, and Hui Wang. 2017. "Identification and Functional Analyses of Novel Antioxidant Peptides and Antimicrobial Peptides from Skin Secretions of Four East Asian Frog Species." *Acta Biochimica et Biophysica Sinica* 49 (6): 550-59.

Wang, Yipeng, Jing Hong, Xiuhong Liu, Hailong Yang, Rui Liu, Jing Wu, Aili Wang, Donghai Lin, and Ren Lai. 2008. "Snake Cathelicidin from *Bungarus Fasciatus* Is a Potent Peptide Antibiotics." *PLOS ONE* 3 (9): e3217.

Wieczorek, Michal, Håvard Jenssen, Jason Kindrachuk, Walter R P Scott, Melissa Elliott, Kai Hilpert, John T J Cheng, Robert E W Hancock, and Suzana K Straus. 2010. "Structural Studies of a Peptide with Immune Modulating and Direct Antimicrobial Activity." *Chemistry & Biology* 17 (9): 970-80.

Wiegand, Irith, Kai Hilpert, and Robert E W Hancock. 2008. "Agar and Broth Dilution Methods to Determine the Minimal Inhibitory Concentration (MIC) of Antimicrobial Substances." *Nature Protocols* 3 (2): 163-75.

Wimley, William C, and Stephen H White. 1996. "Experimentally Determined Hydrophobicity Scale for Proteins at Membrane Interfaces." *Nature Structural Biology* 3 (10): 842-48.

Yan, Jielu, Pratiti Bhadra, Ang Li, Pooja Sethiya, Longguang Qin, Hio Kuan Tai, Koon Ho Wong, and Shirley W I Siu. 2020. "Deep-AmPEP30: Improve Short Antimicrobial Peptides Prediction with Deep Learning." *Molecular Therapy. Nucleic Acids* 20 (June): 882-94.

All publications and patents referred to herein are incorporated by reference. Various modifications and variations of the described subject matter will be apparent to those skilled in the art without departing from the scope and spirit of the invention. Although the invention has been described in connection with specific embodiments, it should be understood that the invention as claimed should not be unduly limited to these embodiments. Indeed, various modifications for carrying out the invention are obvious to those skilled in the art and are intended to be within the scope of the following claims.

What is claimed is:

1. An engineered antimicrobial peptide (AMP) comprising an amino acid sequence selected from the group consisting of:
   FLLKIVALLKKKLL (SEQ ID NO:1) or an antimicrobial peptide having at least 90% amino acid sequence identity thereto,
   FGKLLKLGKGLGG (SEQ ID NO:2) or an antimicrobial peptide having at least 90% amino acid sequence identity thereto,
   FGKLLKLGKGLKG (SEQ ID NO:3) or an antimicrobial peptide having at least 90% amino acid sequence identity thereto,
   FLLKLGLGKKKLL (SEQ ID NO:4) or an antimicrobial peptide having at least 90% amino acid sequence identity thereto,
   FLIKILKGGKGGK (SEQ ID NO:5) or an antimicrobial peptide having at least 90% amino acid sequence identity thereto,
   FIGAIASYLKKFR (SEQ ID NO:6) or an antimicrobial peptide having at least 90% amino acid sequence identity thereto,
   GVVDIIKGAGKKFAKGLAGKIANKK (SEQ ID NO:7) or an antimicrobial peptide having at least 90% amino acid sequence identity thereto, and
   GLMDTVKNAAKNLAGQLLDKIKCKITGC (SEQ ID NO:8) or an antimicrobial peptide having at least 97% amino acid sequence identity thereto;
   wherein the engineered AMP is not naturally occurring.

2. A composition comprising at least one engineered AMP of claim 1.

3. The engineered antimicrobial peptide (AMP) of claim 1, wherein the engineered AMP comprises the amino acid sequence of SEQ ID NO: 1.

4. The engineered antimicrobial peptide (AMP) of claim 1, wherein the engineered AMP comprises the amino acid sequence of SEQ ID NO: 2.

5. The engineered antimicrobial peptide (AMP) of claim 1, wherein the engineered AMP comprises the amino acid sequence of SEQ ID NO: 3.

6. The engineered antimicrobial peptide (AMP) of claim 1, wherein the engineered AMP comprises the amino acid sequence of SEQ ID NO: 4.

7. The engineered antimicrobial peptide (AMP) of claim 1, wherein the engineered AMP comprises the amino acid sequence of SEQ ID NO: 5.

8. The engineered antimicrobial peptide (AMP) of claim 1, wherein the engineered AMP comprises the amino acid sequence of SEQ ID NO: 6.

9. The engineered antimicrobial peptide (AMP) of claim 1, wherein the engineered AMP comprises the amino acid sequence of SEQ ID NO: 7.

10. The engineered antimicrobial peptide (AMP) of claim 1, wherein the engineered AMP comprises the amino acid sequence of SEQ ID NO: 8.

* * * * *

```
                              SEQUENCE LISTING

Sequence total quantity: 11
SEQ ID NO: 1            moltype = AA   length = 14
FEATURE                 Location/Qualifiers
source                  1..14
                        mol_type = protein
                        organism = synthetic construct
SEQUENCE: 1
FLLKIVALLK KKLL                                                              14

SEQ ID NO: 2            moltype = AA   length = 13
FEATURE                 Location/Qualifiers
source                  1..13
                        mol_type = protein
                        organism = synthetic construct
SEQUENCE: 2
FGKLLKLGKG LGG                                                               13

SEQ ID NO: 3            moltype = AA   length = 13
FEATURE                 Location/Qualifiers
source                  1..13
                        mol_type = protein
                        organism = synthetic construct
SEQUENCE: 3
FGKLLKLGKG LKG                                                               13

SEQ ID NO: 4            moltype = AA   length = 13
FEATURE                 Location/Qualifiers
source                  1..13
                        mol_type = protein
                        organism = synthetic construct
SEQUENCE: 4
FLLKLGLGKK KLL                                                               13

SEQ ID NO: 5            moltype = AA   length = 13
FEATURE                 Location/Qualifiers
source                  1..13
                        mol_type = protein
                        organism = synthetic construct
SEQUENCE: 5
FLIKILKGGK GGK                                                               13

SEQ ID NO: 6            moltype = AA   length = 13
FEATURE                 Location/Qualifiers
source                  1..13
                        mol_type = protein
                        organism = synthetic construct
SEQUENCE: 6
FIGAIASYLK KFR                                                               13

SEQ ID NO: 7            moltype = AA   length = 25
FEATURE                 Location/Qualifiers
source                  1..25
                        mol_type = protein
                        organism = synthetic construct
SEQUENCE: 7
GVVDIIKGAG KKFAKGLAGK IANKK                                                  25

SEQ ID NO: 8            moltype = AA   length = 28
FEATURE                 Location/Qualifiers
source                  1..28
                        mol_type = protein
                        organism = synthetic construct
SEQUENCE: 8
GLMDTVKNAA KNLAGQLLDK IKCKITGC                                               28

SEQ ID NO: 9            moltype = AA   length = 34
FEATURE                 Location/Qualifiers
source                  1..34
                        mol_type = protein
                        organism = synthetic construct
SEQUENCE: 9
KRFKKFFRKL KKSVKKRAKE FFKKPRVIGV SIPF                                        34
```

```
SEQ ID NO: 10          moltype = AA  length = 34
FEATURE                Location/Qualifiers
source                 1..34
                       mol_type = protein
                       organism = synthetic construct
SEQUENCE: 10
KRFKKFFKKL KKSVKKRAKK FFKKPRVIGV SIPF                           34

SEQ ID NO: 11          moltype = AA  length = 13
FEATURE                Location/Qualifiers
source                 1..13
                       mol_type = protein
                       organism = synthetic construct
VARIANT                2
                       note = X can be isoleucine or leucine
VARIANT                3
                       note = X can be isoleucine or leucine
VARIANT                5
                       note = X can be isoleucine or leucine
VARIANT                6
                       note = X can be isoleucine or leucine
SEQUENCE: 11
FXXKXXKGGK GGK                                                  13
```